(12) United States Patent
Zheleznyak et al.

(10) Patent No.: US 11,382,795 B2
(45) Date of Patent: Jul. 12, 2022

(54) APPARATUS AND METHOD FOR ENHANCING CORNEAL LENTICULAR SURGERY WITH LASER REFRACTIVE INDEX CHANGES

(71) Applicant: University of Rochester, Rochester, NY (US)

(72) Inventors: Leonard Zheleznyak, Pittsford, NY (US); Scott Catlin, Pittsford, NY (US)

(73) Assignee: University of Rochester, Rochester, NY (US)

( * ) Notice: Subject to any disclaimer, the term of this patent is extended or adjusted under 35 U.S.C. 154(b) by 1021 days.

(21) Appl. No.: 15/653,891

(22) Filed: Jul. 19, 2017

(65) Prior Publication Data

US 2018/0021172 A1 Jan. 25, 2018

Related U.S. Application Data

(60) Provisional application No. 62/364,285, filed on Jul. 19, 2016.

(51) Int. Cl.
 *A61F 9/008* (2006.01)

(52) U.S. Cl.
 CPC ........ *A61F 9/00814* (2013.01); *A61F 9/0084* (2013.01); *A61F 9/00804* (2013.01); *A61F 9/00827* (2013.01); *A61F 9/00829* (2013.01); *A61F 9/00838* (2013.01); *A61F 2009/0088* (2013.01); *A61F 2009/00842* (2013.01); *A61F 2009/00846* (2013.01); *A61F 2009/00848* (2013.01); *A61F 2009/00872* (2013.01);
 (Continued)

(58) Field of Classification Search
 CPC .............. A61F 9/00814; A61F 9/00804; A61F 9/00827; A61F 9/00829; A61F 9/00838; A61F 9/0084; A61F 2009/00842; A61F 2009/00846; A61F 2009/00848; A61F 2009/00872; A61F 2009/00878; A61F 2009/0088; A61F 2009/00895
 See application file for complete search history.

(56) References Cited

U.S. PATENT DOCUMENTS 8,100,530 B2 * 1/2012 Zhou ...................... A61B 3/103
  351/205
8,512,320 B1 * 8/2013 Knox ...................... A61F 9/008
  606/5
(Continued)

FOREIGN PATENT DOCUMENTS

WO 2004105661 A1 12/2004

OTHER PUBLICATIONS

Li et al.: "Mild Decentration Measured by a Scheimpflug Camera and Its Impact on Visual Quality Following SMILE in the Early Learning Curve," The Association for Research in Vision and Ophthalmology, Inc., www.iovs.org, ISSN: 1552-5783, pp. 3886-3892 (2014).
(Continued)

*Primary Examiner* — Lynsey C Eiseman
*Assistant Examiner* — Amanda L Steinberg
(74) *Attorney, Agent, or Firm* — Andrew J. Anderson; Harter Secrest & Emery LLP

(57) ABSTRACT

Methods and systems wherein laser induced refractive index changes by focused femtosecond laser pulses in optical tissues is performed in combination with corneal lenticular surgery to achieve overall desired vision corrections.

31 Claims, 11 Drawing Sheets

(52) U.S. Cl.
CPC .............. *A61F 2009/00878* (2013.01); *A61F 2009/00895* (2013.01)

(56) References Cited

U.S. PATENT DOCUMENTS

| | | | |
|---|---|---|---|
| 8,956,344 B2 | 2/2015 | Russman et al. | |
| 9,545,340 B1 | 1/2017 | Knox et al. | |
| 9,814,567 B2* | 11/2017 | Peyman | A61F 9/00804 |
| 2004/0243111 A1 | 12/2004 | Bendett et al. | |
| 2009/0005764 A1* | 1/2009 | Knox | A61F 9/00804 |
| | | | 606/5 |
| 2011/0071509 A1 | 3/2011 | Knox et al. | |
| 2013/0338650 A1* | 12/2013 | Jester | A61F 9/00804 |
| | | | 606/5 |
| 2014/0058367 A1* | 2/2014 | Dantus | A61F 9/00802 |
| | | | 606/6 |
| 2014/0128857 A1* | 5/2014 | Wottke | A61F 9/008 |
| | | | 606/5 |
| 2016/0364543 A1* | 12/2016 | Dupps, Jr. | G06F 19/00 |

OTHER PUBLICATIONS

"VisuMax femtosecond system" brochure; Carl Zeiss Meditec AG Pub. No. 00000-2031-103 VMX.4710; www.meditec.zeiss.com (2012).

* cited by examiner

FIG. 13A
FIG. 13B
FIG. 14A
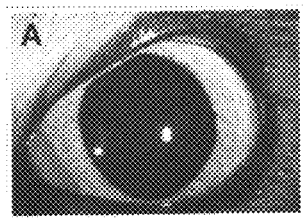
FIG. 14B
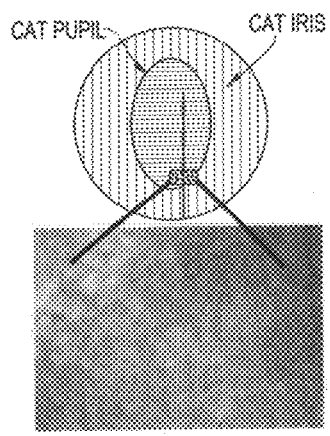
FIG. 14C
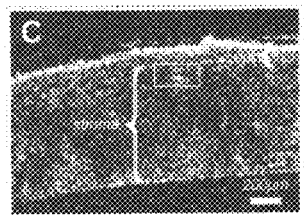

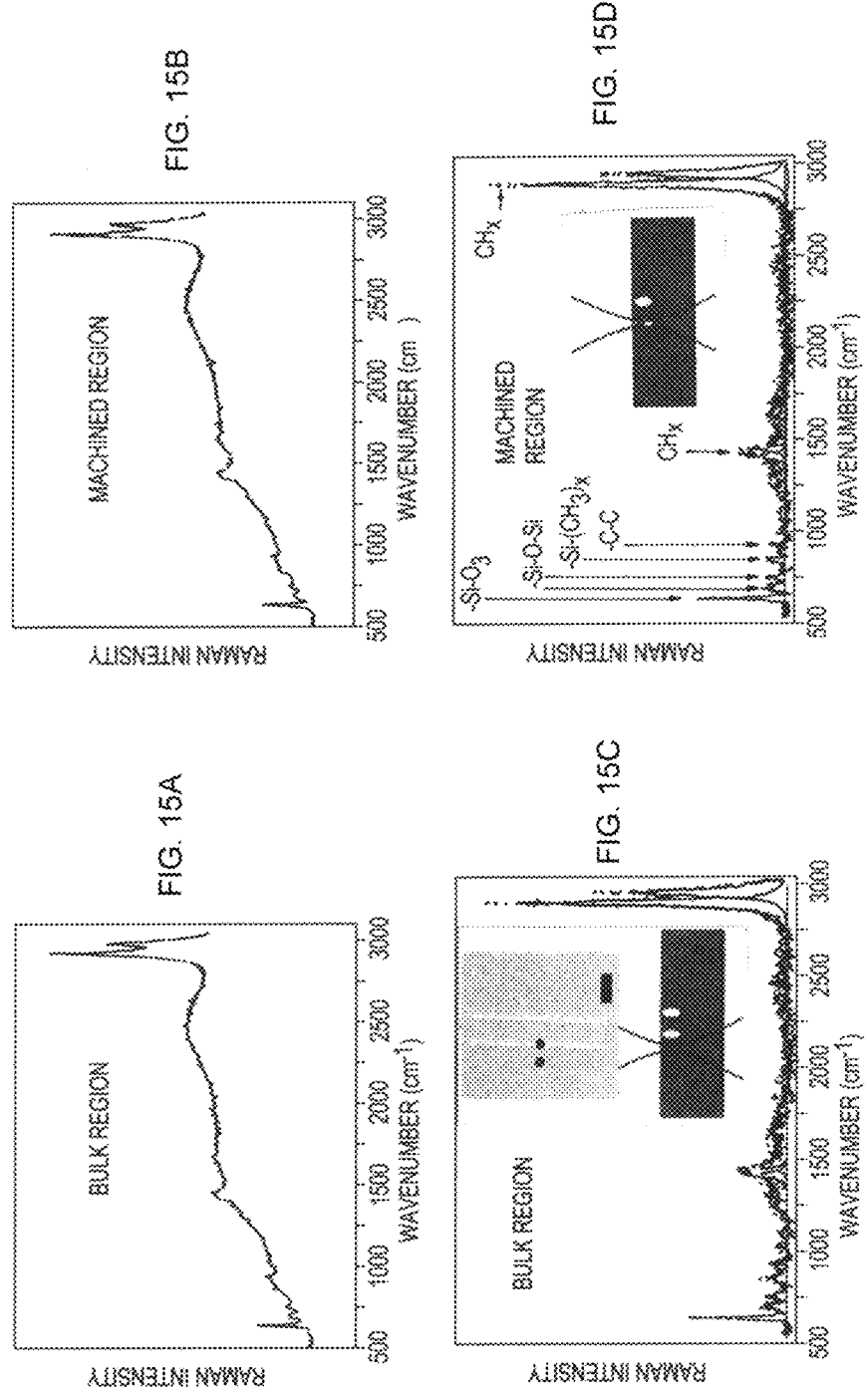

APPARATUS AND METHOD FOR ENHANCING CORNEAL LENTICULAR SURGERY WITH LASER REFRACTIVE INDEX CHANGES

CROSS REFERENCE TO RELATED APPLICATIONS

This application claims the benefit under 35 USC 119(e) of Provisional Patent Application No. 62/364,285 filed Jul. 19, 2016, the disclosure of which is hereby incorporated by reference herein in its entirety.

FIELD OF THE INVENTION

The present invention is directed to vision correction and more particularly to vision correction by a combination of corneal lenticular surgery and modifying the index of refraction of ocular tissue in the eye by a high-repetition, low-pulse energy femtosecond laser.

BACKGROUND

Surgical apparatus for generating cut surfaces in the cornea of an eye in order to correct ametropia, such as described, e.g., in WO 2004/105661 and U.S. Pat. No. 8,956,344, the disclosures of which are incorporated herein by reference in their entireties, comprises a laser unit, which can focus pulsed laser radiation for generating cut surfaces into the cornea and move the radiation therein, and a control unit, which controls the laser unit for generating cut surfaces such that a predetermined lenticle to be removed is separated from the surrounding corneal material in the cornea by at least one cut surface. Such references further describe a method for generating cut surfaces in the cornea of an eye in order to correct ametropia, wherein the pulsed laser radiation for generating cut surfaces is focused into the cornea and moved therein such that a predetermined lenticle to be removed is separated from the surrounding corneal material in the cornea by at least one cut surface. These are examples of laser small incision lenticle extraction (SMILE) systems. However, as further described in U.S. Pat. No. 8,956,344, the desired correction of ametropia of the eye is frequently not achieved by such apparatus and method due to the effect of the cut surface. Decentration, in particular, has been noted as one mild effect that may result in undesirable side effects, such as halos, glare, monocular diplopia, and a reduction in visual acuity, as reported by Meiyan Li et al. in "Mild Decentration measured by a Scheimpfug Camera and its Impact on Visual Quality Following SMILE in the Early Learning Curve", The Association for Research in Vision and Ophthalmology, Inc., www.iovs.org, ISSN: 1552-5783, pp. 3886-92 (2014). While U.S. Pat. No. 8,956,344 teaches that at least two mutually spaced apart cut surfaces may be formed as opening cuts, each extending from the lenticle to the anterior corneal surface, where the position and shape of the opening cuts are selected such that the opening cuts contribute to the correction of the ametropia of the eye or do not counteract the correction of the ametropia of the eye, such additional surface cuts can introduce additional trauma, and still undesirably contribute to induced ametropia.

Additional possible issues and limitations of lenticular incision surgery include: (i) only relatively gross corrections can be made, as small diopter changes (e.g. 1 D or less of corrections) or fine alterations to correct higher order aberrations or complex surfaces or corrections are not generally achievable; (ii) aberrations may be induced—for example coma and astigmatism, but it may induce other aberrations as well, such as spherical aberration or trefoil or mixed astigmatism; (iii) issues with centering the lenticle may lead to decentration of the desired correction; and (iv) multiple surgical incisions and removal of corneal material may cause biomechanical weaknesses in the cornea.

U.S. Pat. No. 8,512,320, the disclosure of which is incorporated herein by reference in its entirety, discloses a method for correcting vision in a patient by modifying the refractive index of cornea tissue. The method comprises identifying and measuring the degree of vision correction of the patient; and determining the position and type of refractive structures to be written into the cornea tissue of the patient to correct the patient's vision. The refractive structures are written by irradiating select regions of the cornea tissue with focused laser pulses having a wavelength in the visible or near-IR, e.g., from 400 nm to 900 nm, and a pulse energy from 0.01 nJ to 10 nJ. The refractive structures are characterized by a positive change in refractive index in relation to non-irradiated cornea tissue of the patient. Such process may be referred to as Intra-tissue Refractive Index Shaping (IRIS) in biological tissues.

SUMMARY

The present disclosure is directed towards methods and systems wherein laser induced refractive index changes by focused femtosecond laser pulses in optical tissues is performed in combination with corneal lenticular surgery to achieve overall desired vision corrections.

In a particular embodiment, a method for correcting vision in a patient is described, comprising:

(a) generating cut surfaces in a cornea of an eye in order to correct ametropia using an apparatus, said apparatus comprising: a first laser unit, which focuses first pulsed laser radiation into the cornea and moves said focused radiation therein in order to generate cut surfaces within the cornea; and a control unit, which controls the first laser unit for generating cut surfaces such that a predetermined lenticle to be removed is separated from the surrounding corneal material within the cornea by at least one cut surface; and (b) modifying the refractive index of ocular tissue of the eye, by irradiating select regions of the ocular tissue with a focused, visible or near-IR second laser below the optical breakdown threshold of the tissue to provide refractive structures that exhibit a change in refractive index, and exhibit little or no scattering loss, and scanning over the select regions with the second laser such that ablation or removal of the tissue is not observed in the irradiated region.

In particular embodiments, the lasers from the IRIS and SMILE procedures may or may not be the same in many respects. For example IRIS could be done at 400 nm wavelength, whereas SMILE is typically at 1043 nm. However, they could be done more closely at 800 nm or 1030 nm for IRIS, with SMILE at 1030-1043 nm. Alternatively, both IRIS and SMILE may be done between about 750-1045 nm, or more preferably between about 780-800 nm or about 1030-1045 nm, or at about 800 nm or about 1030-1045 nm, so it may be possible to combine the systems—either with or without the same lasers or wavelengths. Each of IRIS and SMILE can further optionally be done at other additional specific wavelengths.

In particular embodiments, IRIS may be performed before, after or simultaneous with SMILE on a given eye.

In particular embodiments, the same laser may be used for both, while a two-photon photosensitizer may be added as target for IRIS, before or after SMILE procedure, to enhance sensitivity and enable lower laser power. Tunable lasers may be used to achieve the various wavelength ranges, and/or harmonic generators may be used to double native laser wavelengths to achieve these wavelengths.

In particular embodiments, relatively gross refractive corrective changes may be achieved in a given eye with SMILE (e.g., sphere and cylinder corrections), then diagnostics (e.g., wavefront aberrometry, topography, corneal thickness, etc.) may be used to determine any further refinements to sphere, cylinder or higher order aberrations that are then corrected with IRIS. In addition, IRIS could be used to create a custom treatment pattern to correct all of the individual aberrations and visual acuity reducing aspects of the eye post-SMILE, typically by employing a post-SMILE diagnostic (for example, aberrometry or topography) to define all visual acuity reducing issues, and then creating an IRIS treatment pattern to counteract or reduce those collected issues. There could be a waiting period in between procedures to ensure "settling" and "stabilizing" of the first procedure.

In further embodiments, the lenticle removed in the SMILE procedure is used for testing of IRIS corneal response to ensure exact individualized IRIS parameters. Testing of the lenticle material may be done before or after removal of lenticle—followed by diagnostic measurements on the altered lenticle. For example, interferometry or aberrometry or biomechanical testing may be completed in order to determine if the measured IRIS changes match the expected or target change defined by the parameters set in doing an IRIS treatment on the lenticle. Then any measured or identified difference between the measured IRIS treatment in the lenticle and the target IRIS treatment can be used to refine as needed the IRIS parameters to be applied in creating the visual correction in the remaining corneal tissue to ensure exact corneal response in corneal treatment thereafter.

In particular embodiments, IRIS may be used to correct remaining lower and higher order aberrations post-SMILE, and in particular post-SMILE induced vertical coma and/or astigmatism, which comes from the superior corneal incision (window to remove the SMILE tissue). In other words, IRIS procedures can correct the eye's aberrations which: 1a) were induced by SMILE (e.g. vertical coma or astigmatism); or 1b) are not correctable by SMILE (e.g. large magnitudes of defocus and cylinder, higher order aberrations like spherical aberration, coma, trefoil, etc.).

In particular embodiments, SMILE process is used to only make monofocal refractive corrections, while IRIS is additionally used to: 2a) write a diffractive multifocal pattern to increase the eye's depth of focus post-SMILE (e.g., write a Fresnel lens pattern w/half wave phase change); 2b) write a refractive multifocal to increase the eye's depth of focus (e.g., zonal refractive, central add power); or 2c) apply 2a and/or 2b for a binocular modified monovision presbyopia correction.

In particular embodiments, the IRIS refractive element or refractive index change layer is written anterior to the SMILE incision; while in other embodiments it may be written on either side of the SMILE incision (anterior or posterior).

In further embodiments, IRIS refractive index change may strengthen the cornea (e.g., via induced corneal or chemical crosslinking) which may be used to help prevent biomechanical complications post-SMILE, such as ectasia. In such embodiments, an additional flat wavefront (like piston) may be written across the cornea for increased strength purposes, in addition to writing any desired optical correction features.

In particular embodiments, where a photosensitizer dopant is desired to be employed to enhance 2-photon absorption during the IRIS procedure, the photosensitizer dopant (e.g. riboflavin or NaFl) may be added via topical drops, and/or injected into the SMILE pocket through the SMILE incision, thereby going around the epithelium and enhancing sensitization of the optical tissue in photosensitized-IRIS procedures.

BRIEF DESCRIPTION OF THE DRAWINGS

FIGS. 13A and 13B show slit lamp imaging of the cornea, showing the penetration of a chromophore;

FIGS. 14A-14C show IRIS in the unfixed cat cornea;

FIGS. 15A-15D show the effects on the Raman spectrum; and

DETAILED DESCRIPTION

Lenticular Incision Surgery Description

Figure 1:
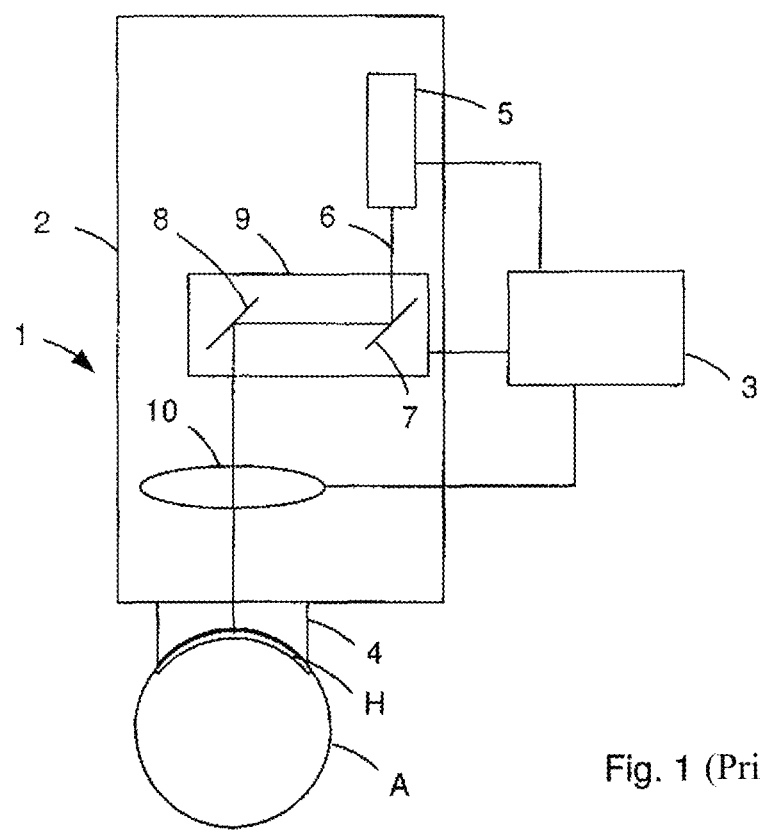
FIG. 1 shows a schematic view of an embodiment of an apparatus for corneal lenticular surgery which may be employed in accordance with the present disclosure.

Lenticular incision surgery methods and apparatus as described in U.S. Pat. No. 8,956,344, incorporated by reference above, include an apparatus for generating cut surfaces in the cornea of an eye in order to correct ametropia in that the position and shape of the opening cuts are selected such that the opening cuts contribute to the correction of the ametropia of the eye or do not counteract the correction of the ametropia of the eye. While the following description of lenticular surgery is more specifically in the context of the improvements described in U.S. Pat. No. 8,956,344, the present description is not limited to such improvements, and applies to lenticular incision surgery techniques in general. As described in U.S. Pat. No. 8,956,344, the opening cuts themselves, although being very small, may lead to an undesirable deterioration of the eye's ametropia. The apparatus described therein for generating cut surfaces in the cornea of an eye in order to correct ametropia is said to advantageously benefit from the fact that an opening cut, which is to be provided and through which the lenticle can be removed, is also simultaneously taken into account with respect to the correction of the eye's ametropia. It has turned out that favorable results can be achieved by providing two or more opening cuts. Providing two or more opening cuts has the advantage that they can be used, for example, to rinse the area being operated on (cut area of the lenticle).

Further, the inclusion of the opening cuts in the correction of ametropia is advantageous insofar as the lenticle volume to be removed can be minimized. Thus, reductions in thickness from several μm up to 100 μm can be achieved. This allows, for example, minimizing mechanical weakening of the cornea, if such weakening is caused by material removal or lenticle removal, respectively.

The opening cuts are typically provided such that it is not possible to fold back a corneal lamella as in the known LASIK operation (laser in situ keratomileusis). Thus, the opening cuts do not lead to a flap of the type provided and folded back in the LASIK operation.

The ametropia to be corrected may be, for example, myopia, hyperopia, astigmatism or presbyopia. It is also possible for the present invention to correct higher-order errors of refracting power. In particular, fourth-order errors of refracting power (spherical aberrations) lead to problems with night vision. Thus, these errors of refracting power of the cornea, or ametropias, can also be corrected by the apparatus according to the invention.

The control described in U.S. Pat. No. 8,956,344 may control the laser unit to thereby generate at least three mutually spaced apart opening cuts such that the centers of area of the opening cuts coincide with the corners of a regular polygon. In this case, it is possible, for example, that the opening cuts do not cause additional astigmatism.

The geometrical shape may be the same for each opening cut for the procedure, although it is also possible to select different geometrical shapes. Thus, for example, the control unit may control the laser unit such that the cut length of at least one opening cut from the anterior corneal surface to the lenticle differs from the cut length of the other opening cuts.

Further, the control unit may control the laser unit to generate exactly two mutually spaced apart opening cuts such that the centers of area of the opening cuts are located on a straight line which, when viewed in a top view of the eye, is parallel to one axis of astigmatism of the eye or intersects said axis at a maximum angle of 10°. This enables a correction for astigmatism. Preferably, the steepest axis of astigmatism is selected (i.e., that axis in relation to which the greatest astigmatism is present).

The control unit can control the laser unit such that at least one of the opening cuts, when viewed in a top view of the eye, has the geometrical shape of a circular ring segment. This shape can be realized with particular ease using conventional laser units in ophthalmic correction apparatuses.

In particular, the control unit can control the laser unit such that the opposite straight sides of the circular ring segment enclose an angle of 30°-120°, 45°-80°, or 30°-60°.

Further, the control unit can control the laser unit such that the opposite straight sides of the circular ring segment have a length of 0.1-1 mm or 0.2-0.4 mm, when viewed in a top view.

In the apparatus, the control unit can control the laser unit such that a further cut surface is provided as a relieving cut, which extends from the anterior co-meal surface into the cornea, but not up to the lenticle. The location and shape of the relieving cut may be selected so as to contribute to the correction of the eye's ametropia. Of course, several relieving cuts can be provided. Due to the additional relieving cut or cuts, an effective correction of ametropia can be achieved.

The control unit can control the laser unit such that at least one of the cut surfaces is generated as a perforated cut surface. A perforated cut surface is understood herein to be a cut surface which is not entirely continuous, but comprises material bridges which break away under a predetermined mechanical load (for example, by removal of the lenticle).

In a method of the above-mentioned type, the location and shape of the opening cuts are selected such that they contribute to the correction of the eye's ametropia or do not counteract the correction of the eye's ametropia.

Using the method, it is therefore possible to provide the required opening cuts such that they contribute to the correction of ametropia or do not counteract the correction of ametropia. This makes it possible to minimize the material volume of the lenticle to be removed. In particular, the lenticle need not be provided, for example, to compensate for imaging errors caused by the opening cuts, which would otherwise disadvantageously lead to a greater material volume to be removed from the cornea.

In the method, the position and shape of the opening cuts may be selected such that the correction of the ametropia of the eye is not counteracted in such a manner that the opening cuts do not generate additional astigmatism of the eye. This makes it possible to correct myopia or hyperopia in which the patient, while no longer being near-sighted or far-sighted, has an ametropia in the form of an astigmatism.

The ametropia to be corrected may be myopia, hyperopia, astigmatism and/or presbyopia. The ametropia may further comprise higher-order errors of refracting power, as well. In particular, the ametropia may include fourth-order errors of refracting power such as spherical aberration, which plays a major role in night vision capacity.

In the method, at least three mutually spaced apart opening cuts can be generated such that their centers of area coincide with the corners of a regular polygon. In this case, it is probable that the opening cuts will not cause additional astigmatism.

The cut length of at least one opening cut from the anterior corneal surface to the lenticle may be made to differ from the cut lengths of the other opening cuts. The opening cuts may also have the same or differing geometrical shapes and/or dimensions.

In one method, exactly two mutually spaced apart opening cuts can be generated such that their centers of area are located on a straight line which, when viewed in a top view of the eye, is parallel to an axis of astigmatism of the eye (preferably the steepest axis of astigmatism) or intersects said axis at a maximum angle of 10°. Such spaced apart opening cuts enable effective correction of astigmatism.

These opening cuts may be executed such that at least one of the opening cuts, when viewed in a top view of the eye, has the geometrical shape of an circular ring segment. Such a shape can be easily realized using a laser unit of a conventional ophthalmic correction apparatus.

In particular, the opening cut may be carried out such that the opposite straight sides of the circular ring segment enclose an angle of 300-120°, 45°-80°, or 30°-60°.

Further, the at least one opening cut may be carried out such that opposite straight sides of the circular ring segment have a length of 0.1-1 mm or 0.2-0.4 mm.

In one present method, a further cut surface may be formed as a relieving cut, extending from the anterior cornmeal surface into the cornea, but not up to the lenticle. The position and shape of the relieving cut may be selected such that the cut contributes to the correction of the ametropia. One or several mutually spaced apart relieving cuts can be formed, the opening cut(s) enable(s) improving correction of ametropia.

In one present method, at least one of the cut surfaces may be formed as a perforated cut surface, thereby resulting in smoother cut surfaces, as compared to cut surfaces produced as continuous cut surfaces by pulsed laser radiation.

In particular, one method of this disclosure allows the lenticle separated from the surrounding corneal material to be removed from the cornea through one of the opening cuts.

It is further possible to divide the lenticle into two or more parts by the pulsed laser radiation and to remove said parts of the lenticle from the cornea through one or more opening cuts.

Further, the opening cuts may also be used to effect flushing of the cut surfaces or, where applicable, to introduce drugs.

Further, a method is described for generating control data for a control unit of a correcting apparatus for generating cut surfaces in the cornea of an eye. The correcting apparatus may comprise a laser unit and a control unit. The laser unit may focus pulsed laser radiation into the cornea in order to generate cut surfaces and move said radiation therein. The control unit for the laser unit generates control data, thereby allowing the control unit to control the laser unit, on the basis of the control data to generate cut surfaces, such that a predetermined lenticle to be removed is separated from the surrounding corneal material in the cornea through at least one cut surface and such that at least two mutually spaced apart cut surfaces are provided as opening cuts. Each opening cut may extend from the lenticle to the anterior corneal surface. The position and shape of the opening cuts may be predetermined by the control data, such that the opening cuts contribute to correction of the ametropia of the eye or do not counteract the correction of the ametropia of the eye.

The method for generating control data may be further embodied such that further embodiments of the disclosed method for generating cut surfaces in the cornea of an eye in order to correct ametropia can be carried out.

The cut surfaces may be generated in the cornea using the apparatus according to the present disclosure and the present method by pulsed laser radiation. Several processes may take place in the tissue within a time sequence. These processes may be initiated by pulsed laser radiation. If the power density of the radiation is above a threshold value during any pulse, an optical breakthrough may appear, which, for example, would form a plasma bubble in the cornea. Such optical breakthrough threshold may in general also be referred to as Laser Induced Optical Breakdown. The plasma bubble then grows, due to expanding gas after the optical breakthrough has formed. If the optical breakthrough is not maintained, the gas generated in the plasma bubble is absorbed by the surrounding tissue, and the bubble disappears. Tissue-separating effects, acting without plasma bubbles, are also possible. For the sake of simplicity, all such processes, including their effects, are summarized here by the term "optical breakthrough."

For tissue separation to occur, the laser radiation may be applied in pulsed form, with the pulse duration usually being below 1 ps. Thus, the power density required for the respective pulse to initiate the optical breakthrough is achieved within a narrow spatial area. High focusing of the laser beam in combination with the short pulses allows the optical breakthrough to be placed in the cornea with pinpoint accuracy. For cut surface generation, a series of optical breakthroughs is generated at the corresponding locations for the cut surface.

It will be appreciated that the features mentioned above and those yet to be explained below can be used not only in the indicated combinations, but also in other combinations or alone, without departing from the scope of the present invention.

FIGS. 1-8 herein correspond to FIGS. 1-8 of U.S. Pat. No. 8,956,344 incorporated by reference herein above. In the embodiment shown in FIG. 1, the apparatus 1 for generating cut surfaces in the cornea H of an eye A in order to correct ametropia comprises a laser unit 2 and a control unit 3 for control of the laser unit 2. Further, the apparatus 1, which is also referred to hereinafter as a correcting apparatus, may comprise a contact element 4 which is detachably coupled with the laser unit 2 and with which the eye A to be corrected is in contact during operation of the apparatus 1.

As is evident from the schematic representation of FIG. 1, the laser unit 2 comprises a laser 5 emitting pulsed laser radiation 6. In this case, the pulse duration is, for example, in the femtosecond range (e.g. 50-800 fs) at a pulse repetition frequency of between 10 and 1 MHz.

The pulsed laser radiation 6 is focused through the contact element 4, by two deflecting mirrors 7, 8 forming a scanner 9 and by optics 10, into the cornea H of an eye A contacting the contact element 4 and is moved in the cornea H. This is effected under the control of the control unit 3, so that basically any locations in the cornea can have the pulsed laser radiation 6 applied thereon.

Of course, the scanner may also be designed in any other manner known to the person skilled in the art.

The control unit 3 may control the laser unit 2 such that an optical breakthrough for tissue separation is generated at the respective focus location in the cornea H. The focus locations are selected to be adjacent each other such that a desired cut surface can be generated in the cornea H. The focus locations may be adjacent each other such that the tissue is cut through completely between the focus locations. However, it is also possible that small tissue bridges remain, so that the cut surface can be referred to as a perforated cut surface.

The laser unit 2 and the control unit 3 are shown in a schematic and simplified manner in FIG. 1. Thus, for example, the optics 10, depicted as a lens, may comprise several optical elements, suitably arranged along the beam path from the laser 5 to the contact element 4.

Figure 2:
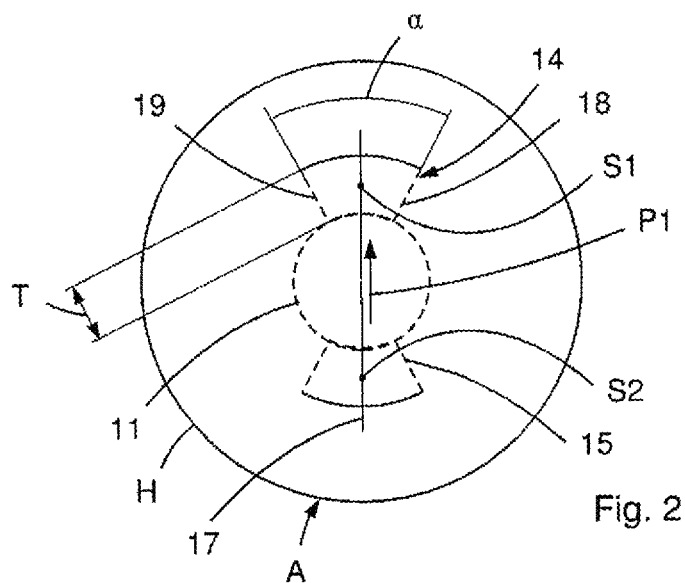
FIG. 2 shows a top view of an eye after carrying out a method as disclosed for generating cut surfaces in the cornea of an eye for correction of ametropia.
Figure 3:
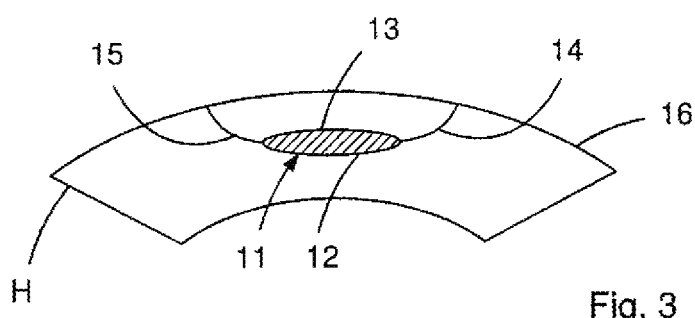
FIG. 3 shows a cross-sectional view of the cornea H along the line 17 of FIG. 2.

The correction apparatus 1 may be operated such that, in order to correct ametropia (in this case, for example, correction of myopia and astigmatism), a preferably lens-shaped partial volume 11 (hereinafter also referred to as a lenticle) in the cornea H, as shown in FIGS. 2-8, is separated from the surrounding corneal material by the pulsed laser radiation 6. This is preferably carried out such that first the rear surface 12 (FIG. 3) of the lenticle 11 and then the front surface 13 of the lenticle 11 is cut. In order to allow the lenticle 11, separated from the residual corneal material, to be removed from the cornea H, first and second opening cuts 14, 15, each extending from the lenticle 11 to the anterior corneal surface 16, are provided, as schematically shown in FIGS. 2 and 3.

The lenticle 11 can then be removed from the cornea H in a known manner through the first or second opening cut 14, 15. Due to the missing corneal volume (lenticle 11), the cornea will change its shape in this area. Prior to carrying out the method, the shape of the lenticle was selected such that the shape of the cornea after removal of the lenticle results in the desired correction of ametropia.

In the described exemplary embodiment of FIGS. 2 and 3, two opening cuts 14 and 15 have been performed and the shapes and positions of the opening cuts 14 and 15 are selected such that any still existing astigmatism of the eye A is also corrected thereby.

In other words, the invention takes into consideration the fact that even the very small opening cuts 14 and 15 may have an influence on the astigmatism of the eye A. This per se undesired effect is used in the invention to correct an existing astigmatism of the eye A.

In the described exemplary embodiment, it is assumed that the steepest axis of astigmatism in FIG. 2 extends from top to bottom as indicated by the arrow P1. In this case, the two opening cuts 14 and 15 are arranged such that their centers of area S1 and S2 are located on a straight line 17, which is parallel to or coincides with, the axis of astigmatism P1. Merely for the sake of clearer illustration, FIG. 2 shows the axis of astigmatism P1 slightly laterally of the straight line 17.

By this arrangement of the opening cuts 14 and 15, the astigmatism of the eye A is reduced due to the opening cuts 14 and 15.

As is evident from FIG. 2, the opening cuts 14 and 15, when viewed in the top view of FIG. 2 are respectively provided as circular ring segments. Since both opening cuts 14 and 15 are identical, only the first opening cut 14 will be described in more detail below.

The two straight sides 18 and 19 of the opening cut 14 have the same length T (FIG. 2), said length being between 0.1 and 1 mm or between 0.2 and 0.4 mm in the exemplary embodiment described here. Further, the two straight sides 18 and 19 enclose an angle $\alpha$, which may range from 30°-120° or from 40°-80°.

Figure 4:
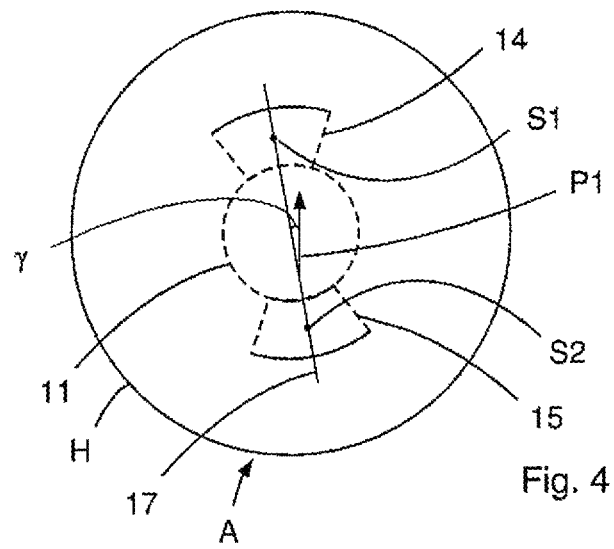
FIG. 4 shows a top view of an eye after carrying out a method of the disclosure according to another embodiment.

FIG. 4 shows a modification of the embodiment of FIGS. 2 and 3. In this modification, the opening cuts 14 and 15 are placed such that the straight line 17 connecting the centers of area S1, S2 encloses an angle 7 with the axis of astigmatism P1, said angle being 10° here. Even with this modification, an excellent correction of astigmatism is still achieved by the opening cuts 14 and 15.

Figure 5:
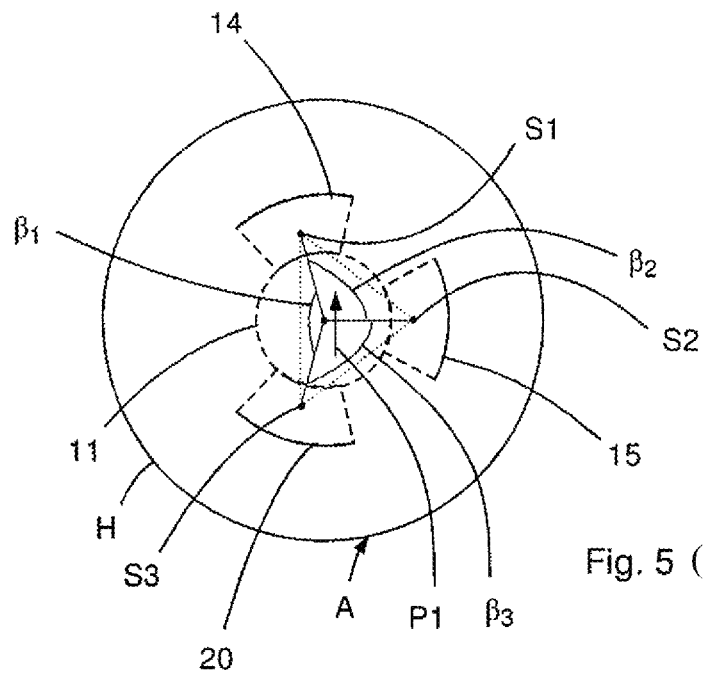
FIG. 5 shows a top view of an eye after carrying out a method of the disclosure according to yet another embodiment.

As is evident from the embodiment shown in FIG. 5, three opening cuts 14, 15 and 20 have been carried out. The opening cuts 14, 15 and 20 are mutually spaced apart, with the centers of area S1, S2 and S3 defining a triangle, which is indicated by a dotted line in FIG. 5.

In order to achieve a correction of astigmatism by the opening cuts 14, 15 and 20, the opening cuts 14, 15 and 20 are located at unequal angular distances from one another on the circumference of the lenticle 11, as is evident from FIG. 5. Thus, the angle $\beta_1$ is 150° and the angles $\beta_2$ and $\beta_3$ are each 105°. Due to this asymmetrical angular distribution of the opening cuts 14, 15 and 20, the desired correction of astigmatism is achieved.

Figure 6:
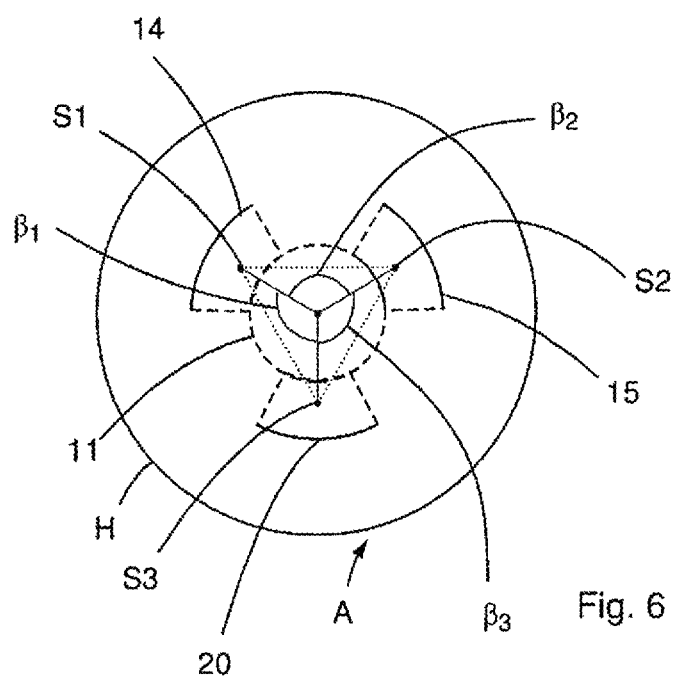
FIG. 6 shows a top view of an eye after carrying out a method of the disclosure according to another embodiment.

However, it is also possible to distribute the opening cuts 14, 15 and 20 at equal angles, as shown in FIG. 6. In this case, the angles $\beta_1$, $\beta_2$ and $\beta_3$ are each 120°. This distribution of the opening cuts is selected if no correction of astigmatism by the opening cuts 14, 15 and 20 is desired. This may be the case, for example, if no astigmatism, but only a myopia has to be corrected. Thus, the opening cuts 14, 15 and 20 can be provided such that there is no influence on the astigmatism. As is evident from FIG. 6, the triangle defined by the centers of area S1, S2 and S3 is then an equilateral triangle.

Further, it is possible for the opening cuts 14, 15 and 20 in FIG. 6 to be arranged and shaped such that they contribute to the desired correction of myopia.

Figure 7:
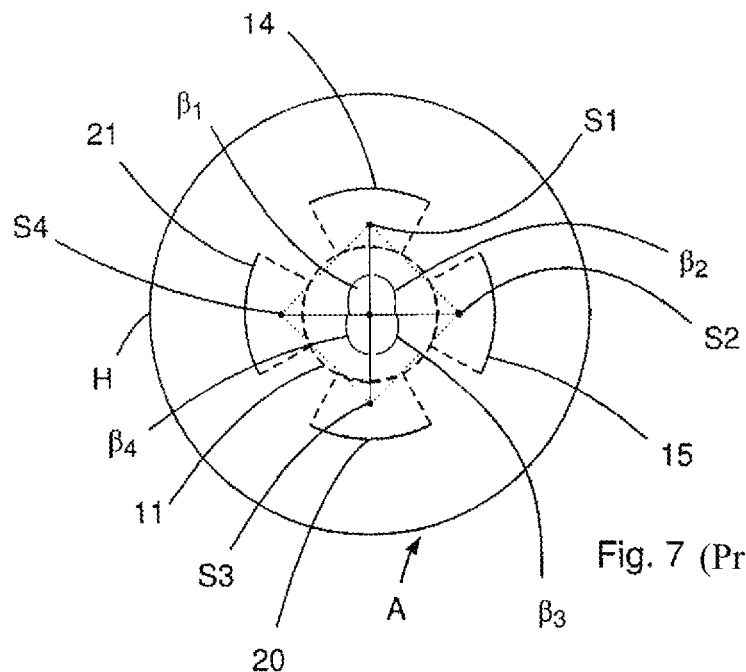
FIG. 7 shows a top view of an eye after carrying out a method of the disclosure according to yet another embodiment.

Providing the opening cuts without influencing the astigmatism of the cornea H is also possible in the case of four opening cuts, as shown in FIG. 7. The four opening cuts 14, 15, 20 and 21 are again distributed at equal angles on the circumference of the lenticle 11 so that, in this case, the centers of area S1, S2, S3 and S4 define a square.

In general, it can be said that n opening cuts (with n>2) can be provided such that their centers of area form a regular n-sided polygon so as to cause no influence on astigmatism by the n opening cuts.

Figure 8:
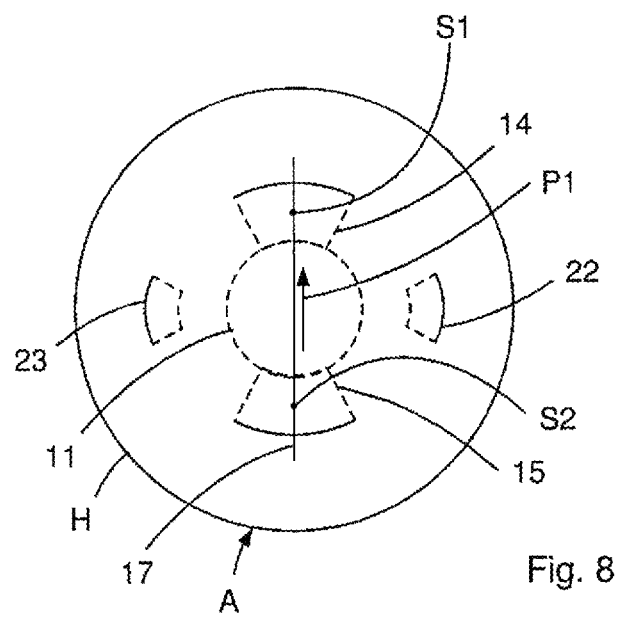
FIG. 8 shows a top view of an eye after carrying out a method of the disclosure according to another embodiment.

As indicated in FIG. 8, which shows a further development of the embodiments of FIGS. 2 and 3, relieving cuts 22, 23 can be carried out in addition to the opening cuts 14, 15, said relieving cuts extending from the anterior surface of the cornea H into the latter, but not up to the lenticle 11. These relieving cuts 22, 23 can be used in order to correct the ametropia to be corrected by the lenticle 11 and/or of the astigmatism (arrow P1).

Laser Induced Refractive Index Change (IRIS) Description

Choosing the right laser parameters is critical for achieving IRIS in biological tissues. Not only does the femtosecond laser fluence at the objective focus have to be below the optical breakdown threshold of the tissue, it also has to be strong enough to induce some nonlinear changes, and the scan speed must be set within an effective range. In the past two decades, extensive experimental and theoretical work has been done to characterize laser-induced optical breakdown thresholds in different materials, including the cornea (Docchio, Sacchi & Marshall, 1986, Du, Liu, Korn, Squier & Mourou, 1994, Giguere et al., 2007, Loesel et al., 1996, Stern, Schoenlein, Puliafito, Dobi, Birngruber & Fujimoto, 1989, Stuart, Feit, Rubenchik, Shore & Perry, 1995, Tien, Backus, Kapteyn, Murnane & Mourou, 1999, Vogel et al., 2005) and the lens (Brazitikos, D'Amico, Bochow, Hmelar, Marcellino & Stangos, 1998, Li & Borkman, 1990, Vogel, Capon, Asiyo-Vogel & Birngruber, 1994). However, most of this work centered on the use of continuous wave (CW) lasers or on single pulses from low-repetition-rate lasers in which thermal diffusion time is much shorter than the time interval between adjacent pulses. Thus, each pulse is responsible for a change in the material. Indeed, it has been established that for pulses longer than 10 ps, the optical breakdown threshold fluence scales as the square root of the pulse duration (Du et al., 1994). For pulses shorter than 10 ps but longer than about 100 fs (which is the case with IRIS settings), the experimental results show a departure from this dependence. However, whether threshold fluence increases or decreases as pulse durations get shorter remains a challenging question (Stern et al., 1989, Stuart et al., 1995, Tien et al., 1999). Some models predict that the threshold would first increase, then decrease when pulse duration becomes shorter than 100 fs, but there is no solid experimental evidence to support this (Tien et al., 1999). More recently, it has been claimed that for corneal stroma, the breakdown threshold is almost plateau-like when the pulse duration is between 100 fs and 1 ps, with a rapid decrease in threshold for pulse durations in the low end of the femtosecond range (Giguere et al., 2007). However, insufficient experimentation on cornea and lens using sub-100 fs pulses makes it difficult to support this prediction and furthermore, existing data were collected using single pulses from low-repetition-rate lasers.

When high-repetition-rate femtosecond laser pulses are used, cumulative, free-electron-mediated chemical effects, photochemical bond breaking and thermal effects contribute to the laser-tissue interaction. As a result, the breakdown threshold fluence may be quite different from that predicted by current models (Vogel et al., 2005). Several studies on the effects of high-repetition-rate femtosecond lasers on fused silica and borosilicate glass have found that laser pulses greatly increased the temperature of the materials at the laser focus (Eaton, Zhang, Herman, Yoshino, Shah, Bovatsek & Arai, 2005a). Vogel calculated the temperature change in water would be >10° K with a 0.6 NA focusing lens and 100 fs laser pulses (Vogel et al., 2005), assuming that with each pulse, an energy density of 1 $J/cm^3$ at the center of the initial temperature distribution is deposited. Using very high-repetition-rate (93 MHz), ultra-short laser pulses (27 fs), the optical breakdown threshold for the 0.70 NA focusing condition in lightly-fixed corneal stroma and lens cortex was found to be 55 mW and 75 mW average laser power respectively (Ding et al., 2008). This corresponds to 0.6 nJ and 0.8 nJ pulse energies respectively, both lower than the optical breakdown power reported by König and colleagues using 1 nJ pulse energy, 170 fs pulse duration and 1.30 NA focusing in porcine corneas (König et al., 2002). By using 30 mW and 45 mW average laser power (0.3 nJ and 0.5 nJ pulses), it is able to induce IRIS, without accompanying photo-disruption and tissue destruction.

Preliminary experiments demonstrated, for the first time, that it is possible to cause low-scattering-loss, refractive index modifications in lightly-fixed cat cornea and lens using 93 MHz repetition rate, 27 fs laser pulses with 0.3 nJ and 0.5 nJ pulse energies. These modifications were visible only using DIC microscopy and were not associated with apparent tissue damage. They represent refractive index changes between 0.005±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) were observed to persist for up to one year, even after drying and rehydration of the hydrogel (Ding, Cancado, Novotny, Knox, Anderson, Jani, Blackwell, Künzler & Smith).

Even relatively small refractive index changes induced in cornea and lens tissue can have a significant impact on optical power. Based on published values for the power (39 D) and native refractive index (1.376) of the cat cornea (Hughes, 1977), IRIS should generate a change in corneal power ranging between 0.14 D and 0.56 D (assuming an index change between 0.005 and 0.02). Similarly, for the cat lens (power=53 D, refractive index of the homogeneous lens=1.554) (Hughes, 1977), the refractive index changes induced by micromachining should theoretically alter lenticular power by between 0.5 D and 0.7 D. It may be possible to achieve refractive index changes that are either positive or negative, although changes in the cornea typically have been shown to be positive.

Improvement in refractive index change and/or writing speeds may be achieved by employing a laser wavelength in a range for which the optical tissue is more inherently sensitive to 2-photon absorption. US 20110071509, the disclosure of which is incorporated herein by reference in its entirety, e.g., discloses more particularly a method for forming a refractive structure in a living eye, where the method includes the steps of directing and focusing a plurality of femtosecond laser pulses in a spectral region between about 350 nanometers (nm) to about 600 nm, and more particularly blue light, within a cornea or a lens of the living eye; controlling the intensity of the laser pulses to have an intensity sufficient to change the refractive index of the cornea or lens within a defined focal region, but below a damage threshold the cornea or lens, or at a level that will not photo-disrupt cornea or lens tissue outside of the focal region; and forming a refractive structure in the focal region of the cornea or the lens by scanning the laser pulses through a volume of the cornea or the lens. Each refractive structure is characterized by a change in refractive index, and exhibits little or no scattering loss.

Additionally or alternatively, a photosensitizer may be employed to chemically enhance the two-photon absorption properties of both tissues. Such photosensitization can result in at least a doubling of the refractive index changes and a several hundred fold increase in the micromachining speeds attained. The use of a photosensitizer is more specifically disclosed U.S. Pat. No. 9,545,340, the disclosure of which is incorporated by reference herein in its entirety. The photosensitizer may include a chromophore having a two-photon, absorption cross-section of at least 10 GM at the laser wavelength employed, and in particular embodiments a two-photon, absorption cross-section of at least 10 GM between a laser wavelength range of 750 nm to 1100 nm. Some multiphoton or two-photon absorbers may include fluorescein, coumarin or riboflavin.

Ongoing experiments in our laboratories have generated information about the cellular and molecular mechanisms underlying IRIS in the living cornea, and allowing us to gain critical knowledge that can be used to further manipulate the size, placement and design of micromachined patterns, as well as the magnitude of the refractive index changes with which they are associated. The ability to alter the native refractive index of the cornea and lens without causing significant tissue damage has important theoretical and practical implications. By understanding how laser power can be used to alter tissues non-destructively, and by understanding the nature of these alterations, an entirely new branch in the field of laser biology can be opened up. Among other things, this could completely change approaches to laser refractive surgery, and to vision correction more generally. For instance, the preservation of tissue clarity during the treatment allows the application of IRIS for the creation of corneal fiducial markings that could be used to align eye trackers during LASIK, and for refractive corrections in a closed-loop approach, e.g. with specific benefit for the correction of higher-order aberrations, as well as for "touch-up corrections" of ocular surface defects. More broadly, the feasibility of IRIS in living tissues offers new possibilities for non-invasive alterations, marking or pattern-inscription within living organisms. From a theoretical stand-point, it also provides a unique opportunity to better understand and define the extent to which we can optically manipulate even large areas of living tissues without inducing a significant wound healing reaction.

Various ranges of parameters are particularly useful in implementing IRIS in the present disclosure. In treatment of the eye, the laser wavelength should be such that the tissues through which laser pulses pass are transparent to the pulses. There should also be no damage to the retina; any change should be confined to the tissue located at the spot of focus of the pulses. Also, for non-destructive alteration of ocular tissue, a $CO_2$ laser or excimer laser should not be used, since there should be no ablation or removal of the tissue.

A laser pulse frequency (repetition rate) of 93 MHz is useful for many applications. A preferable range is from 1 MHz to 10 GHz, and more preferably from 10 to 500 MHz.

Linked to the pulse frequency is the average power. A preferable range is from 1 to 1,000 mW, and more preferably 10 to 100 mW, and more preferably still from 50 to 60 mW. The energy of each pulse should preferably be less than 1 nJ and more preferably less than 0.5 nJ, although a range from 0.01 to 10 nJ and more preferably from 0.1 to 2 nJ can be used.

A laser pulse width of 30 fs is useful for many applications. A preferable range is from 5 fs to 1 ps, and more preferably from 10 to 500 fs, or from 10 to 100 fs, 100-300 fs, or 200-500 fs.

The scanning speed of the laser is preferably at least 0.4 μm/s, more preferably at least 0.1 mm/s, at least 1 mm/s, at least 10 mm/s, or at least 100 mm/s, and in various embodiments can range, e.g., up to 50 mm/s, up to 100 mm/s, up top 600 mm/s, up to 800 mm/s, or even higher, e.g., up to 1 m/s. For example, scan speeds of 100 mm/s, 200 mm/s, 400 mm/s, 700 mm/s and even higher and all speeds in between are valuable and have been demonstrated and are effective to reduce the treatment time.

The wavelength should be one to which the tissues through which the laser pulses must pass are transparent. It should also preferably be just barely within the visible range for the patient, or outside of the visible range (e.g., near-infrared), so as not to bother the patient. A wavelength of 800 nm is useful; preferable ranges include 600-1,000 nm (and more preferably 700-900 nm) and above 1,000 nm (e.g., 1000-1300 nm). Wavelengths in the range of 350-550 nm are also useful in particular embodiments.

The laser pulses are focused to a spot size that is preferably about 1 μm. Preferable ranges include 0.5 μm to 2, 10, or 50 μm. The spot size may also be elongated with a cross-section (i.e. perpendicular to the optical axis) in the ranges of 1-10 microns, and a length parallel to the optical axis of 1-50 microns, or more preferably 5-30 microns, or about 10-20 microns. The NA of the focusing lens may be 0.2 or higher, for example 0.2-1.0, or 0.2-0.6.

Various structures can be produced in the ocular tissue. Examples include high refractive index structures such as Bragg gratings, microlens arrays, optical zone plates, diffractive multifocals or diffractive monofocals, and Fresnel lenses. Additionally, corrections to sphere and cylinder may be included, as well as corrections for various aberrations, such as coma, spherical, chromatic, trefoil, can be included.

A preferred embodiment of IRIS as may be performed in the present invention will now be set forth in detail with reference to the drawings.

Preliminary experiments (Ding, Huxlin & Knox, 2007, Ding et al., 2008, Huxlin, Ding & Knox, 2008) showed that it is possible to change the refractive index of the lightly-fixed, mammalian cornea and lens without tissue destruction, a phenomenon termed Intra-tissue Refractive Index Shaping (IRIS). To achieve this, first measured, then reduced femtosecond laser pulse energies below the optical breakdown threshold of lightly-fixed post-mortem cat corneas and lenses. In both silicone and non-silicone-based hydrogels, this approach induced a significant change in refractive index without visible plasma luminescence or bubble formation (Ding et al., 2006).

Eight corneas and eight lenses were extracted under surgical anesthesia from five normal, adult domestic short-hair cats (felis cattus). To avoid decomposition and opacification prior to femtosecond laser micromachining, extracted feline tissues were immediately drop-fixed for 10 minutes (corneas) or one hour (lenses) in a solution consisting of 1% paraformaldehyde in 0.1M phosphate buffered saline (PBS), pH 7.4. Lenses were then cut into 500 μm thick slices using a HM650V vibratome (Microm International), after which lens sections and whole corneas (also ~500 μm thick) were immersed in a mixture of 30% ethylene glycol+ 30% sucrose in 0.1M PBS, pH7.4 at 4° C. Storage in this solution minimized tissue swelling and loss of transparency. Small pieces of tissue, ~1 $cm^2$ were then flattened onto a clear glass slide (1×3 inches, 1 mm thick, Surgipath Medical Industries Inc., IL). In the case of corneal pieces, this was done with the epithelium facing up and the endothelium facing down. A glass coverslip (Corning No. 0211 Zinc Titania glass) was placed on the top of each piece, stabilizing it for the duration of the experiment. The ethylene glycol/ sucrose storage solution was used as mounting medium to minimize dehydration of the cornea and lens tissue samples since these effects are known to alter the refractive index and transparency of both these tissues (Fisher, Masiello, Goldstein & Hahn, 2003, Meek, Dennis & Khan, 2003, Patel, Alio & Perez-Santonja, 2004).

Femtosecond laser micro-machining was conducted as previously described in hydrogels (Ding et al., 2006). The laser source was a Kerr-lens mode-locked Ti: Sapphire laser (K-M Labs). The laser oscillator generated pulses averaging 300 mW, 27 fs in duration, with a 93 MHz repetition rate at 800 nm wavelength. A continuously variable, metallic, neutral density filter inserted into the optical path, was used to adjust the incident laser power onto each cat cornea and lens piece. Pulses were focused 100 μm below the tissue surface using a 60×, 0.70 NA Olympus LUCPlanFLN microscope objective with an adjustable working distance of 1.5-2.2 mm. Because the large amount of glass within the microscope objective induced significant chromatic dispersion into the femtosecond laser pulses, broadening the pulse durations, a standard extra-cavity-prism double-pass configuration was used to compensate for the dispersion and maintain the ultra-short pulse duration. By carefully adjusting this dispersion compensator, we obtained nearly transform-limited 27 fs duration pulses at the focal point of the focusing objective, as measured by a collinear auto-correlator using 3rd order surface harmonic generation (Meschulach, Barad & Silberberg, 2003, Squier, Fittinghoff, Barty, Wilson, Muller & Brakenhoff, 1998). During IRIS, the slide containing the biological tissue samples was mounted on a 3D scanning platform consisting of a Physik Instrumente P-622.2CD XY scanning stage with 250 μm travel range and 0.7 nm close-loop resolution, and a Newport VP-25XA linear servo Z-axis scanning stage with 25 mm travel range and 100 nm resolution. An infrared CCD camera was used to monitor the micromachining process and the generation of visible plasma luminescence in real-time.

A first step was to establish thresholds for the optical breakdown of lightly-fixed feline cornea and lens. The neutral density filter was first adjusted to minimize the focused incident laser power on the cornea and the lens below their breakdown thresholds (Giguere et al., 2007, Loesel et al., 1996). Adjusting the neutral density filter then progressively increased the incident laser power. The breakdown threshold power was reached when visible plasma luminescence suddenly appeared and strong scattering light as well as laser-induced damage became visible (FIGS.

9A-9D). With a 0.70 NA long-working-distance objective, the measured breakdown thresholds for cat cornea and lens were ~55 mW and 75 mW average laser power respectively, which corresponds to pulse energies of 0.6 nJ and 0.8 nJ.

FIGS. 9A-9D: Femtosecond IRIS in lightly-fixed cat corneal stroma just around the tissue breakdown threshold. 9A,9C: Differential interference contrast (DIC) images of lines created in the stroma of two different, lightly-fixed cat corneas with 0.6 nJ pulses and a scanning speed of 10 μm/s. Note dark spots of tissue destruction and "bubbles" (arrowed) along the micromachined lines (clear, horizontal lines within stromal tissue). 9B,9D: Bright Field (BF) images of the corneal region in 9A,9C illustrating the visibility of dark spots of tissue destruction (arrowed) and the relative invisibility of the rest of the lines that are clearly seen under DIC conditions (see 9A,9C).

Figure 10A:
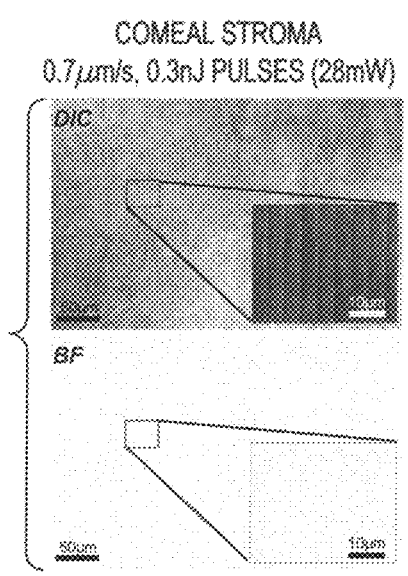
FIGS. 10A and 10B show femtosecond IRIS in a lightly fixed cat corneal stroma and lens cortex below the tissue breakdown threshold.
Figure 10B:
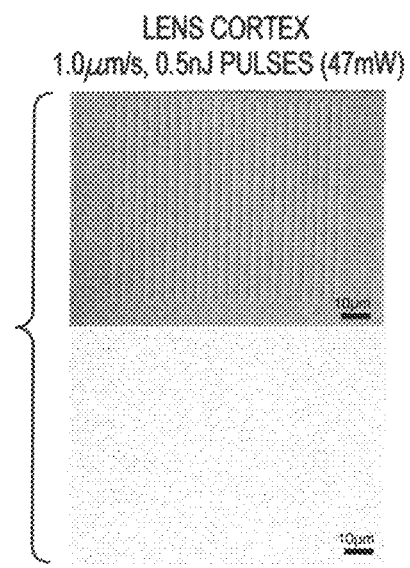

Once tissue breakdown thresholds were established, the focused laser power was lowered gradually by carefully adjusting the neutral density filter until lines could be micromachined without the induction of bubbles or burns (FIGS. 10A and 10B). Average laser power settings at which this could be done were 30 mW in the cornea and 45 mW in the lens, corresponding to pulse energies of about 0.3 nJ and 0.5 nJ respectively. These values lay between those used for imaging and our measured breakdown thresholds. The gratings were micromachined in the horizontal plane within the stromal layer of each corneal piece and the cortex of each lens at a constant speed of 0.7 μm/s for the cornea and 1 μm/s for the lens. The spherical aberration at the laser focus induced by refractive index mismatch was compensated by adjusting the correction collar of the focusing microscope objective in order to achieve the smallest possible laser-affected region along the laser propagation direction (Ding et al., 2006).

Figure 9A:
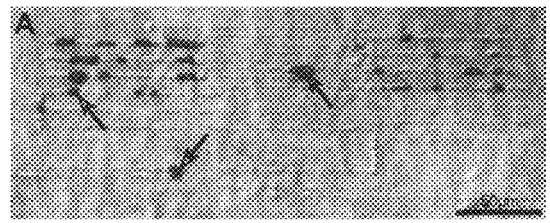
FIGS. 9A-9D show femtosecond IRIS in a lightly fixed cat corneal stroma just around the tissue breakdown threshold.
Figure 9B:
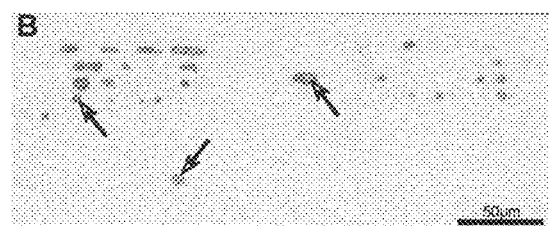
Figure 9C:
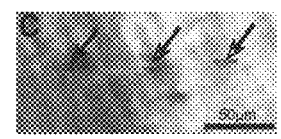
Figure 9D:
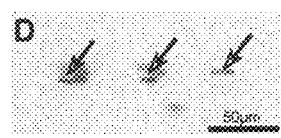

Exposure of lightly-fixed cat corneal and lenticular tissue to 0.3 nJ or 0.5 nJ femtosecond laser pulses (28 mW or 47 mW average laser power) respectively resulted in the reliable creation of line gratings about 100 μm below the epithelial surface or 100 μm below the lens surface in all test samples (FIGS. 10A and 10B). When imaged immediately after micromachining, individual grating lines could be clearly observed and distinguished with differential interference contrast (DIC) microscopy, but they were practically invisible when viewed under bright field (BF) transmission microscopy (BF images in FIGS. 10A and 10B). This could be interpreted as the grating lines having very low scattering properties, which is in contrast to the destructive tissue changes observed with laser pulse energies above the optical breakdown threshold of the tissues (FIGS. 9A-9C). Using the knife-edge method (Smith, 2000), ascertained that the laser focus diameter was 2.5 μm in air, which was much bigger than the micromachined line-widths. Thus, it appears that only the central part of the laser focal area had sufficient intensity to modify corneal and lens tissues.

FIGS. 10A and 10B: Femtosecond IRIS in lightly-fixed cat corneal stroma and lens cortex below the tissue breakdown threshold. 10A: The top photomicrographs are DIC images of a periodic line grating created using 0.3 nJ pulses and a scanning speed of 0.7 μm/s into the stromal layer of a cat corneal piece. Note the absence of tissue destruction (no brown spots). The insert shows a magnified portion of the grating. The bottom photographs are bright field (BF) images of the corneal regions shown the DIC pictures. Note the poor visibility of the micromachined gratings under transmitted, bright light microscopy, which contrasts with the high visibility of the brown spots created when using laser power above the tissue breakdown threshold (see FIGS. 9A-9C). 10B: DIC image of a periodic line grating created using 0.5 nJ pulses and a scanning speed of 1 μm/s in a piece of lens cortex. Note the absence of tissue destruction (no brown spots). The BF image shows the lens region illustrated in the DIC picture.

To assess whether the gratings generated in corneal and lens pieces were associated with a change in refractive index, the slides containing the tissue were first placed under an Olympus BX51 optical microscope where gratings were localized using DIC imaging. A low-power 632.8 nm He—Ne laser was then used to irradiate the gratings (FIGS. 11A and 11B), generating a diffraction pattern that was captured by a digital camera and used to calculate the refractive index changes attained, as described previously (Ding et al., 2006).

Figure 11A:
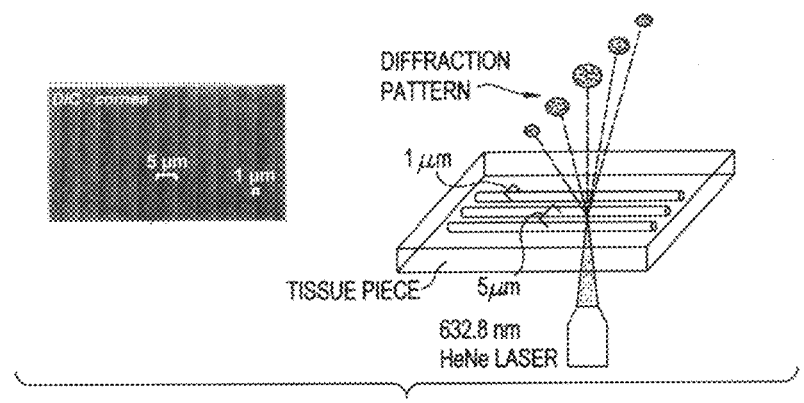
FIGS. 11A and 11B show measurement of the refractive index change in IRIS-treated corneas and lenses immediately after the treatment.
Figure 11B:
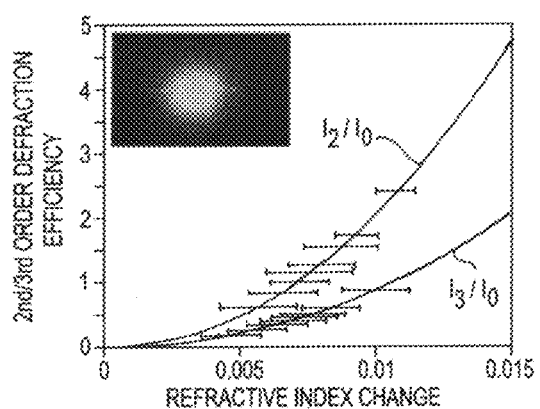

FIGS. 11A and 11B: Measuring refractive index change in IRIS-treated corneas and lenses immediately after the treatment. 11A: DIC image of a periodic line grating created using 0.3 nJ pulses and a scanning speed of 0.7 μm/s in the stromal layer of a piece of cat cornea and subsequently illuminated with a 632.8 nm He—Ne laser to generate diffraction patterns (as shown in 11B) that were used to calculate the change in refractive index attained. 11B: Graph plotting the 2nd and 3rd order diffraction efficiencies and the corresponding laser-induced refractive index changes of eight gratings micromachined in different corneal samples immediately after they were created. The insert is a photograph of the diffraction pattern obtained when illuminating the grating shown in 11A with a 632.8 nm He—Ne laser.

In brief, a power meter measured the intensity of the $0^{th}$-$3^{rd}$ order diffracted light from the gratings and the different order diffraction efficiencies were obtained by calculating the ratios between the intensity of the $1^{st}$, $2^{nd}$ and $3^{rd}$ to the $0^{th}$ order diffraction light. Since the intensity distribution of the diffraction pattern of a phase grating is proportional to the square value of the Fourier Transform of the transmittance function of the grating (Born & Wolf, 1970), one particular value of refractive index change matches only one particular diffraction efficiency value (Ding et al., 2006). To reduce measurement error of the diffraction order intensities, five measurements were collected on each grating, calculating the average value obtained and its standard deviation. In principle, the spatial distribution of the refractive index change within the micromachined region was a small-scale gradient-index structure. However, for the purpose of the investigation, the index profile was presumed to be uniform within the grating lines, which were only 3 μm deep because the spherical aberration at the focal point was corrected (Ding et al., 2006).

Because displacement of the stromal collagen lamellae as a result of post-mortem corneal swelling could not be completely avoided the scattering effect from the $0^{th}$ order diffraction light was very strong obscuring the $1^{st}$ order diffraction light (Meek et al., 2003). Thus, only the $2^{nd}$ and $3^{rd}$ order diffraction efficiencies of each grating could be measured and used to calculate an approximate refractive index change in corneal pieces (FIG. 11B). Because tissue swelling and opacification were minimal in slices of lens cortex, the $0^{th}$ through $3^{rd}$ order diffraction light could be measured clearly and $1^{st}$ and $2^{nd}$ order diffraction efficiencies were used to calculate the induced refractive index change. Although single diffraction efficiency is usually sufficient to calculate refractive index, $1^{st}/2^{nd}$ or $2^{nd}/3^{rd}$ combinations were measured to confirm that the index changes calculated were consistent through different diffraction orders, assuming that the refractive index of cat corneal stroma and lens cortex were 1.376 and 1.400 respectively (Hughes, 1977). For corneal stroma, the index changes induced by the laser in multiple samples ranged between 0.005±0.001 and 0.01±0.001 (FIG. 11B). For cat lens cortex, index changes were larger, ranging between 0.015±0.001 and 0.021±0.001. More recent experiments have shown refractive index changes in tissue as high as 0.03 or 0.05 or higher, with even higher amounts in ophthalmic lens polymers.

After micromachining, each cornea and lens piece was stored in the ethylene glycol/sucrose solution at 4° C. After one month, each piece was re-mounted onto a new glass slide for imaging and a repeat of the diffraction light intensity measurements. This allowed assessing whether the RI change initially observed had been maintained during storage. The first observation was that although the storage solution significantly slowed corneal swelling and opacification, it did not completely prevent either. In spite of this, DIC microscopy was able to reveal the grating structures initially micromachined (FIG. 12A).

Figure 12A:
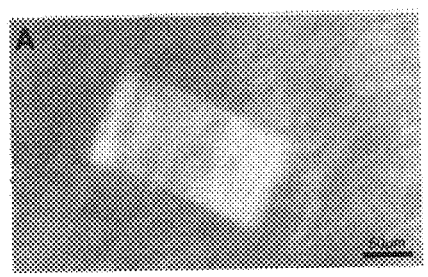
FIGS. 12A and 12B show measurement of the refractive index change in IRIS-treated corneas one month after the treatment.
Figure 12B:
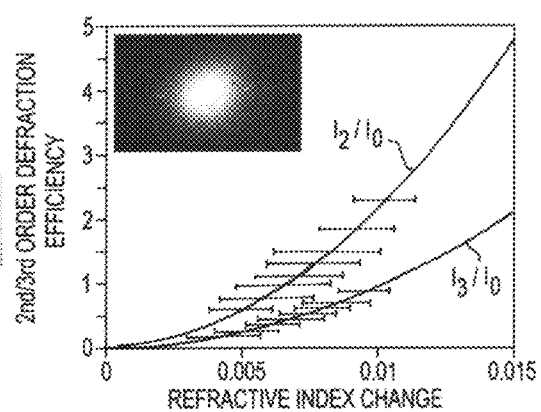

FIGS. 12A and 12B: Measuring refractive index change in IRIS-treated corneas 1 month after the treatment. 12A: DIC image of a periodic line grating created using 0.3 nJ pulses and a scanning speed of 0.7 µm/s into the stromal layer of the cat corneal piece shown in FIGS. 11A and 11B and stored for 1 month. The grating is still visible, but the clarity of its lines is decreased, a likely result of corneal swelling and opacification. 12B: Graph plotting the diffraction efficiencies and the corresponding refractive index changes of eight gratings measured one month after they were created in 8 different corneal pieces. The insert is a photograph of the diffraction pattern obtained when illuminating the grating shown in FIG. 12A with a 632.8 nm He—Ne laser.

For both corneal and lens slices, the diffraction light distribution of one-month old gratings (FIG. 12B) was not significantly different than that obtained right after the gratings' creation (FIG. 11B). In the corneal pieces, the scattering light from the $0^{th}$ order diffraction still obscured the $1^{st}$ order diffraction. However, the $2^{nd}$, $3^{rd}$, and even $4^{th}$ order diffractions were visible and measurable. In the lens pieces, the $1^{st}$, $2^{nd}$ and $3^{rd}$ order diffraction were visible. The refractive index change after one month of storage still ranged between 0.005±0.001 and 0.01±0.001 for corneal pieces and between 0.015±0.001 and 0.021±0.001 for lens slices.

Potentiating IRIS by increasing two-photon absorption (TPA) or other multi-photon absorption of the cornea and lens will now be discussed. In early work with native hydrogels, femtosecond micromachining caused index changes in the range of +0.02 to +0.06, with very slow scanning speeds, as slow as 0.4 microns per second (Ding et al., 2006). The index changes attained in the cat cornea were small (~0.005-0.01) and background scattering made the features difficult to detect. Larger index changes in 500 µm thick slices of cat lens (0.015-0.021) we written, but all at very low scanning speeds (0.7 to 1 µm/s). Such slow scanning speeds severely limit the applicability of the IRIS technique, since the writing of any 3D feature within biological materials would take a prohibitively long time under these conditions.

Figure 12C:
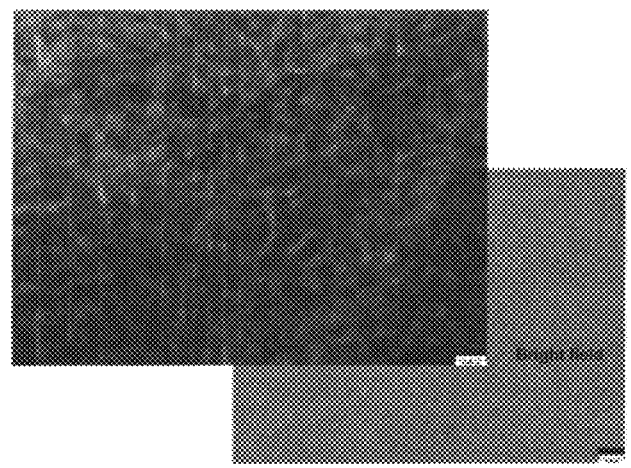
FIGS. 12C-12F show micromachining results in a cornea and a lens with Na-Fluorescein doping.
Figure 12D:
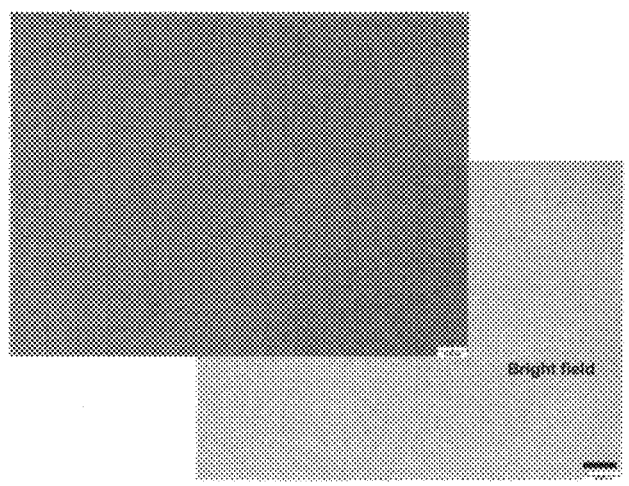
Figure 12E:
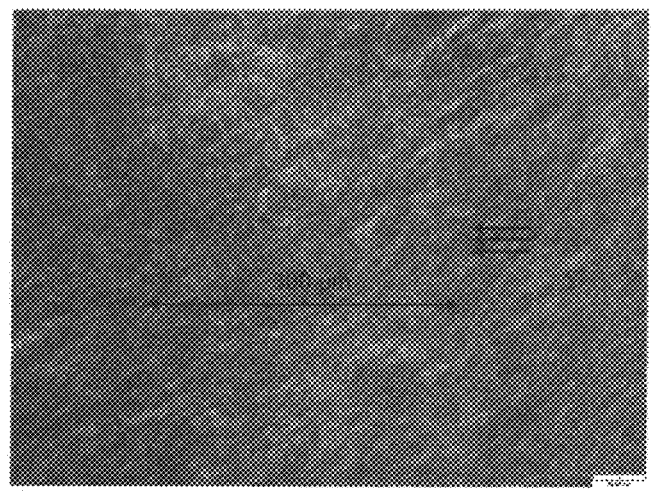
Figure 12F:
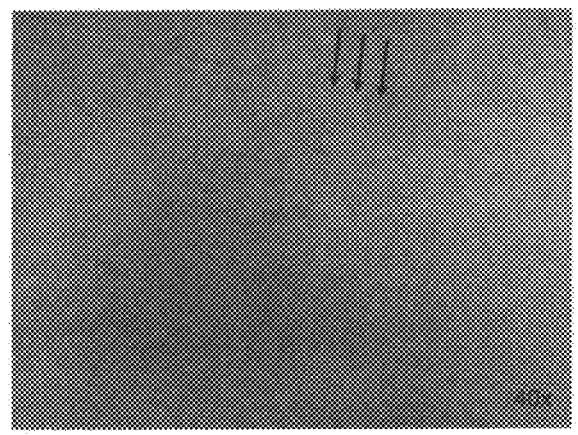

The major reason why writing speeds need to be so slow in the cornea and the lens is that these clear biological tissues possess natively low two-photon absorption (TPA) properties. Thus, it was hypothesized that if the TPA of cornea and lens could be increased through the incorporation of a two-photon absorbing chromophore, this should theoretically increase the rate and magnitude of IRIS in these tissues. Sodium Fluorescein is one such chromophore, which is already commonly used in ophthalmic (and medical) practice. It is non-toxic to the living eye and can even be injected intravenously (e.g. for retinal angiography). To test the hypothesis, lightly-fixed cornea and lens pieces were incubated in a 25% solution of Sodium Fluorescein in ethylene glycol/sucrose/PBS overnight. Both tissue types readily absorbed the chromophore and turned slightly orange. They were then rinsed and IRIS was performed as described above. In Fluorescein-treated cat corneas, scanning speeds of 1 mm/s (~1,400× faster than in non-treated corneas) were attained and used to create multiple lines that were several mm long, and whose refractive index change averaged 0.02 (up to 4× larger than in non-treated corneas). Just as in the non-fluorescein treated corneas, these features were long-lived, lasting through several months of refrigerated storage. FIG. 12C is a phase contrast image showing the refractive index change lines in a cornea doped with 25% sodium fluorescein after micromachining with a scanning speed of 1 mm/s, an average power of 120 mW, a depth below the surface of 120 µm, and a laser wavelength of 800 nm. FIG. 12D is a phase contrast image showing the refractive index change lines in an intraocular lens doped with 25% sodium fluorescein after micromachining with a scanning speed of 1 mm/s, an average power of 100 mW, a depth below the surface of 120 µm, and a laser wavelength of 800 nm. FIG. 12E is a phase contrast image showing a 300 µm wide band micromachined in a doped cat cornea 100 µm below the surface using 20 fs laser pulses, a scanning speed of 1 mm/s, an average power of 120 mW, and a laser wavelength of 800 nm. The image in FIG. 12E was taken right after micromachining. FIG. 12F is an image taken after the fluorescein has been rinsed off.

Femtosecond laser treatment is performed under surgical or topical anesthesia as previously described for conventional laser refractive surgery (Bühren, Yoon, Kenner, MacRae & Huxlin, 2007b, Nagy et al., 2007). The subjects are placed into a specially designed head-mount, which will hold them in a supine position, with the eyes facing directly upwards. A drop of 0.5% Proparacaine Hydrochloride (or other ophthalmic anesthetic agent) will be placed in the eye to be treated. One to two drops of 20% NaFluorescein in a 10% solution of dimethyl sulfoxide (DMSO) in Celluvisc will also be administered to each eye to be treated in order to increase the two-photon absorption rate of the cornea. Pilot experiments show that 10 minutes is sufficient to allow penetration of the fluorescein chromophore through the entire thickness of the cornea (see FIGS. 13A and 13B). Lower and higher concentrations of Na Fluorescein also work, but the amount of time required for penetration increases at lower concentrations. The corneal surface can then be kept moist with the application of saline or ophthalmic moistening agents. Once corneal reflexes have disappeared, the subject can then undergo IRIS treatment over a circular (or otherwise shaped) area 6 mm (or other dimensions, as required) in diameter, in the center (or other location) of its cornea, at a depth of 100 µm (or other depths) below or within the surface epithelium. Other positional parameters can be used if needed. The eye can be kept immobile during the laser treatment by a fixation target or by conjunctival structures, which will be removed at the end of the operation. An infrared CCD camera is used to monitor the micromachining process and the generation of visible plasma luminescence in real-time. The treatment should take about 5-10 minutes per eye, after which the subject will be recovered as clinically prescribed.

FIGS. 13A and 13B: Slit lamp imaging of the cornea of an anesthetized cat with Fluorescein filter, demonstrating penetration of NaFluorescein into the stroma within 10 minutes of its topical application to the eye. 13A: Slit lamp image taken immediately after application of 25% NaFluorescein to the ocular surface. Only the surface epithelium (arrowed) stained. The rest of the corneal depth (approx. to the dotted white line) is completely black. 13B: Slit lamp image of the cornea in FIG. 13A, taken 10 minutes later. The epithelium (arrowed) is still labeled, but now Fluorescein can be seen deeper in the stroma, almost to the endothelium (~dotted line).

A similar protocol, with the major difference being that the Na Fluorescein solution might have to be injected into the anterior chamber of the eye, could be used to enhance TPA in the living lens. IRIS could be performed in the lens by simply using a longer-working-distance focusing objective to focus the femtosecond laser beam into the lens in situ.

In order to assess whether chemical fixation of the cornea with paraformaldehyde was critical to attaining IRIS in the cornea, IRIS on a non-fixed (fresh), post-mortem cat cornea immediately after enucleation was performed. Several small gratings were inscribed one above the other in the corneal stroma and they were imaging with optical coherence tomography (OCT). Several gratings were stacked together in order to make sure that the OCT, with a resolution of ~10 µm, could actually resolve these features, given that individual IRIS lines were only 1-3 µm thick. The results of this experiment was reported at an ARVO meeting (Huxlin et al., 2008) and some pictures are provided in FIGS. 14A-14C. Thus, while fixation may influence the magnitude of RI change attained, IRIS does not actually require it.

FIGS. 14A-14C: IRIS in the unfixed cat cornea. 14A: Front view of the cat eye just prior to excision of the globe. 14B: Schematic diagram of the view of the eye shown in FIG. 14A, illustrating the different visible features (cat iris and pupil) as well as the location of the femtosecond treatment (magnified below in DIC mode) at the bottom of the cornea. The long, black, vertical line through the rectangular IRIS pattern indicates the imaging plane used for optical coherence tomography (OCT). 14C: OCT image of the corneal layers collected through the rectangular IRIS grating (in the plane of the thin black vertical line in FIG. 14B). The IRIS pattern is visible as a thin, horizontal line of increased reflectivity (inside the white rectangle) within the corneal stroma, about 200 µm below the epithelial (epi) surface.

IRIS does not change the Raman spectrum of hydrogels—changes in refractive index, not material composition or chemistry. Balafilcon A hydrogel polymer (Bausch & Lomb, USA) was used for this experiment, whose goal was to gain insight into the mechanisms by which femtosecond micromachining achieved its refractive index change in hydrated, optically clear but non-biological materials. The chemical components of the hydrogel used (Balafilcon A) included tris-(trimethylsiloxy)-silyl propylvinyl carbamate (TPVC), N-vinyl pyrrolidone (NVP) and other types of silicones (Karlgard, Sarkar, Jones, Moresoli & Leung, 2004). Balafilcon A contains 36% water by weight and has an average refractive index of 1.4220 (Ding et al., 2006). The cutoff wavelength of its transmission spectra are within the range of 300 to 350 nm, and its transmissivity at 800 nm is ~83% (Ding et al., 2006). A Kerr-lens mode-locked Ti: Sapphire femtosecond laser oscillator (K-M Labs), generating pulses of 300 mW average power, 27 fs pulsewidth and 93 MHz repetition rate at 800 nm was focused into the hydrogels using a 60×0.70 NA Olympus LUCPlanFLN long-working-distance objective. Throughout the whole experimental process, the hydrogel samples were mounted in a Borate Buffered Saline (BBS) solution between two cover glass slides and maintained their water-content. A 3D scanning platform formed by three Newport VP-25XA linear servo stages with 100 nm resolution was employed to move the hydrogel samples transversely to the direction of the laser beam. Smooth lines 40 µm long were inscribed just below the hydrogel surface using 1.3 nJ pulse-energies, which were below the optical breakdown threshold of the material. These low pulse-energies created a 0.06 refractive index change along the lines. Using the same knife edge method reported previously (Ding et al., 2006), a laser focal diameter of about 2.5 µm was measured. This focal diameter gave rise to laser-irradiated lines about 1 µm wide and 3 µm deep.

In order to check for structural modifications in the machined region, several Raman spectra were measured in 400 nm steps both within and next to the micromachined lines using a 3 mW, 632.8 nm HeNe laser. In both spectra, several Raman peaks were detected over the broad background fluorescence (FIGS. 15A, 15B). Differences in the background fluorescence of the two spectra were first measured since some of the defects generated by MHz femtosecond laser pulses are known to increase fluorescence intensity in fused silica (Reichman, Krol, Shah, Yoshino, Arai, Eaton & Herman, 2006). Here however, no significant changes in background fluorescence were detected. The Raman signal was then calculated by subtracting the background fluorescence from the original spectrum (FIGS. 15C, 15D). The Raman peaks could be assigned to different material bonds activities (see FIG. 15D), but most importantly, the Raman spectra obtained from the machined region were almost identical to the Raman spectra obtained from the untreated regions of hydrogel, suggesting that the micromachining process did not induce significant structural and chemical changes in the hydrogel polymer.

FIG. 15A: Raman spectrum of an untreated (bulk) region of Balafilcon A hydrogel in BBS solution, showing significant background fluorescence over which spectral peaks are superimposed. FIG. 15B: Raman spectrum of one of the fs laser-modified lines inside a Balafilcon A hydrogel piece (see insets in FIG. 15C). FIG. 15C: Raman spectrum of the untreated bulk region of the Balafilcon A hydrogel imaged in FIG. 15A, with background correction. The lower insert illustrates the plane of Raman imaging in a schematic cross section of the modified hydrogel piece photographed above it. The photograph inset is a DIC image of the two micromachined lines. Scale bar=10 µm. FIG. 15D: Raman spectrum of one of the micromachined lines with background correction, showing peaks that are identical in location and magnitude to the adjacent, bulk region imaged in FIG. 15C.

Figure 16A:
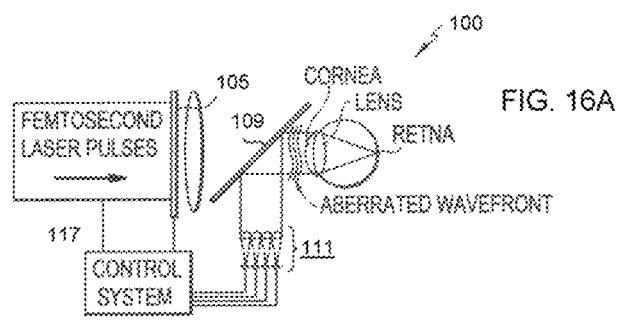
FIGS. 16A-16C show a device on which the preferred or another embodiment can be implemented.
Figure 16B:
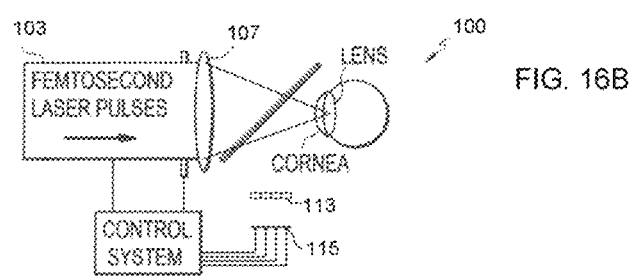
Figure 16C:
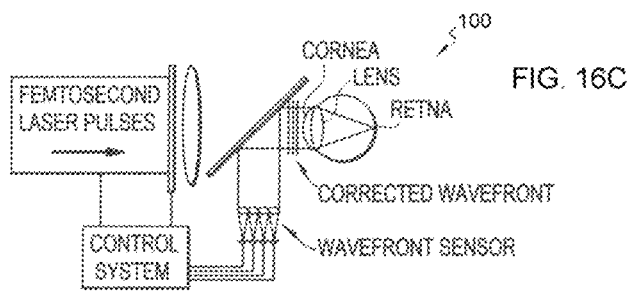

FIGS. 16A-16C show a schematic diagram of a device 100 used to carry out the preferred embodiment or another embodiment. The device 100 includes a laser 103 for emitting femtosecond laser pulses, a shutter 105, a focusing lens 107, a dichroic mirror 109, a wavefront sensor 111 having a lenslet array 113 and a detector array 115, and a control system 117 for controlling the operations described herein.

As illustrated in FIGS. 16A-16C, the process would include the following steps: (1) using a wavefront sensor to detect and measure the lower and higher order aberrations along the optical path of a given eye, (2) calculating the topography and magnitude of refractive index changes required to achieve the necessary aberration correction, (3) focusing the femtosecond laser pulses either into the cornea or intraocular lens in order to carry out the micromachining necessary to induce the required refractive index change. Once the micromachining is complete, the wavefront sensor would be used once again to check the correction of the ocular wavefront. Since the resolution of the femtosecond laser micromachining is about this noninvasive method could be used as a complement or an alternative method for current customized wavefront correction methods.

In FIG. 16A, the shutter 105 is closed for detection of wavefront aberration from the optical path through the wavefront sensor 111, using aberrated light reflected from the retina of the eye. In FIG. 16B, the shutter is open, and light pulses from the femtosecond laser 103 are used to correct the aberration by locally changing the index in the cornea or the lens. In FIG. 16C, after femtosecond laser micromachining, the wavefront correction is verified once again using the wavefront sensor.

Combined SMILE and IRIS Description

As noted above, laser induced refractive index changes by focused femtosecond laser pulses in optical tissues as described herein is performed in combination with corneal lenticular surgery to achieve overall desired vision corrections. IRIS may be performed before, after or simultaneous with SMILE on a given eye. More particularly, relatively gross refractive corrective changes may be achieved in a given eye with SMILE (e.g., sphere and cylinder corrections), diagnostics may then be taken (e.g., wavefront aberrometry, topography, corneal thickness, etc.) to determine any further refinements to sphere, cylinder or higher order aberrations, and the further refinements are then corrected with IRIS. A waiting period may be practiced in between procedures to ensure "settling" and "stabilizing" of the first procedure. Alternatively, the IRIS process may be performed simultaneously with the SMILE process to correct anticipated aberrations typically induced by the SMILE process. In a further embodiment, the IRIS process may be performed prior to the SMILE process, to either correct anticipated aberrations introduced by the SMILE process, or, e.g., to change the refractive index of the tissue at locations defined by the laser focus spot to create corneal fiducial markings for aligning eye trackers during the SMILE process.

As the SMILE incision process and the IRIS refractive index change process may be performed with similar wavelength femtosecond pulse lasers, the systems may be advantageously combined for use with the same laser, e.g., both IRIS and SMILE may be done at 800 nm or ~1030 nm, wherein the laser power and fluence is controlled separately for each process so as to provide required performance. In other embodiments, and in particular where use of different wavelengths are desired for each process, the lasers employed for the IRIS and SMILE procedures may be different. For example IRIS could be done at 400 nm wavelength, whereas SMILE is typically at 1043 nm. Alternatively, both IRIS and SMILE could be done more closely at between about 750-1045 nm, or more preferably between about 780-800 nm or about 1030-1045 nm, or at about 800 nm or about 1030 or 1043 nm. Whether or not the same laser is used for used for both processes, a two-photon photosensitizer may be advantageously added as target for IRIS, before or after SMILE procedure, to enhance sensitivity and enable lower laser power and/or faster writing speeds.

The combination of IRIS and SMILE procedures further advantageously enables testing of IRIS corneal response in the corneal tissue of a given eye to ensure exact individualized IRIS parameters. More particularly, the lenticule removed (or corresponding corneal tissue mass to be removed) in the SMILE procedure may be used for such IRIS corneal response testing. Testing of the lenticule material may thus be done before or after removal of a lenticule from a given eye, and the altered corneal tissue/lenticule may be subject to interferometry or aberrometry or biomechanical diagnostics to determine if lenticular IRIS changes matches the expected change. The diagnostic results may then be used to refine as needed the IRIS parameters to ensure exact corneal response in corneal treatment of the given eye thereafter.

The combination of IRIS and SMILE processes are particularly advantageous in that refractive index changes introduced by IRIS may be used to correct remaining lower and higher order aberrations post-SMILE, and in particular post-SMILE induced astigmatism or vertical coma, which comes from the superior corneal incision (window to remove the SMILE tissue). This may be done in place or, or in addition to, other proposed modifications to the SMILE process designed to decrease induced aberrations such as described in U.S. Pat. No. 8,956,344 incorporated by reference above. In other words, IRIS procedures can correct the eye's aberrations which: 1a) were induced by SMILE (e.g. astigmatism or vertical coma); or 1b) are not correctable by SMILE (e.g. large magnitudes of defocus and cylinder, higher order aberrations like spherical aberration, coma, trefoil, etc); advantageously without the need for performing additional incisions.

In further advantageous combinations, the SMILE process is used to only make monofocal refractive corrections, and IRIS is additionally used to: 2a) write a diffractive multifocal pattern to increase the eye's depth of focus post-SMILE (e.g., write a Fresnel lens pattern w/ half wave phase change); 2b) write a refractive multifocal to increase the eye's depth of focus (e.g., zonal refractive, central add power); or 2c) apply 2a or 2b for a binocular modified monovision presbyopia correction. Such combination takes advantage of the SMILE process to make large corrections, and the IRIS process to fine tune the overall desired optical corrections.

The IRIS refractive element or refractive index change layer may advantageously be written anterior to the SMILE incision, so as to further take advantage of the finer corrections enabled by IRIS processes. In many embodiments, however, the IRIS refractive elements may be written on either side of the SMILE incision (anterior or posterior).

As further described in U.S. Pat. No. 8,956,344, corneal lenticular surgery can result in mechanical weakening of the cornea. The combination of IRIS with SMILE procedures may be advantageous as the IRIS induced refractive index change may help strengthen the cornea (e.g., via induced chemical or tissue crosslinking) which may be used to help off-set the mechanical weakening and prevent biomechanical complications post-SMILE, such as ectasia. An additional flat wavefront (like piston) may be written with a IRIS laser across the cornea for increased strength purposes, e.g., in addition to writing any desired optical correction features.

The combination of IRIS and SMILE procedures are further especially advantageous where a photosensitizer dopant is employed to enhance 2-photon absorption during the IRIS procedure. In such embodiment, the photosensitizer dopant (e.g. riboflavin or NaFl or coumarin, or other two-photon absorbers with an absorption cross-section of at least 10 GM at the laser wavelength employed, and in particular embodiments a two-photon, absorption cross-section of at least 10 GM between a laser wavelength range of 750 nm to 1100 nm) may be added via topical drops opn the surface of the cornea, and/or may be injected directly into the pocket resulting upon removal of the lenticule through the SMILE incision, thereby going around the epithelium and speeding up absorption of the photosensitizer into the target corneal stroma, thus enhancing sensitization of the optical tissue in photosensitized-IRIS procedures and shortening the overall surgical procedure. The photosensitizer alternatively may be injected into the anterior chamber of the eye to achieve adequate penetration into the corneal stroma. Further, patient interfaces (i.e. typically suction rings to immobilize the eye during femtosecond laser treatments, and often including a flat or curved glass component to applanate the cornea) are often used for both SMILE and IRIS procedures. Any of the current patient interfaces may be appended to the laser systems described herein for similar purposes. Additionally, a first SMILE patient interface may be used for the SMILE procedure, and then a different patient interface may be used for the IRIS procedure. For example, a curved SMILE patient interface may be used and a flat IRIS patient interface used for the IRIS procedure. It may also be that the same patient interface is used for both. Further, a photosensitizer for the IRIS procedure may be employed between the two procedures and during a switch between patient interfaces. Alternatively, the photosensitizer may be added to a fluid underneath a patient interface contact glass, polymer or film (such component being either flat or curved, and either in contact with the cornea or non-contacting), in order to allow the photosensitizer to be absorbed into the cornea under pressure from the suction and/or the pressure from the patient interface as a whole.

While a preferred embodiment has been set forth in detail above, those skilled in the art who have reviewed the present disclosure will readily appreciate that other embodiments can be realized within the scope of the invention. For example, numerical values are illustrative rather than limiting, as are recitations of specific equipment and sources. Also, while the preferred embodiment has been disclosed in terms of two-photon absorption, the invention can be implemented through absorption of three or more photons. Therefore, the present invention should be construed as limited only by the appended claims.

We claim:

1. A method for correcting vision in a patient comprising:
    (a) generating cut surfaces in a cornea of an eye using an apparatus comprising a first laser unit and a control unit, wherein the first laser unit focuses first pulsed laser radiation into the cornea and moves said focused radiation therein in order to generate the cut surfaces within the cornea, and wherein the control unit controls the first laser unit to generate the cut surfaces such that a predetermined lenticule to be removed in order to correct ametropia is separated from the surrounding corneal material within the cornea by at least one cut surface, and removing the predetermined lenticule from the cornea to achieve refractive corrective changes in the eye; and
    (b) subsequent to step (a), modifying the refractive index of ocular tissue of the eye to achieve further vision correction in the eye, by irradiating select regions of the ocular tissue with a focused, visible or near-IR second laser below the optical breakdown threshold of the tissue to provide refractive structures that exhibit a change in refractive index, and exhibit little or no scattering loss, and scanning over the select regions with the second laser such that ablation or removal of the tissue is not observed in the irradiated region;
    further comprising testing response of the second laser in the corneal tissue of the eye corresponding to the predetermined lenticule prior to performing step (b), and further comprising performing diagnostics between steps (a) and (b) to determine refinements to sphere, cylinder or higher order aberrations to be corrected in step (b).

2. The method of claim 1, wherein the focused, visible or near-IR second laser has a pulse energy from 0.01 nJ to 10 nJ.

3. The method of claim 1, wherein the first laser and the second laser are the same laser, and wherein the laser power and/or fluence is controlled separately for each of step (a) and step (b) so as to provide required performance.

4. The method of claim 1, wherein the first laser and the second laser have different wavelengths.

5. The method of claim 1, wherein testing response of the second laser in the corneal tissue of the eye corresponding to the predetermined lenticule is performed prior to step (a).

6. The method of claim 1, wherein step (b) is performed to correct aberrations which were induced by step (a), or which are not correctable by step (a).

7. The method of claim 1, wherein step (a) is performed to make monofocal refractive corrections, and step (b) is performed to write a diffractive multifocal pattern to increase the eye's depth of focus, write a refractive multifocal to increase the eye's depth of focus, or both to provide a binocular modified monovision presbyopia correction.

8. The method of claim 1, wherein step (b) further comprises applying a multiple-photon-absorbing chromophore to the optical tissue.

9. The method of claim 8, wherein the multiple-photon-absorbing chromophore comprises a two-photon-absorbing chromophore.

10. The method of claim 9, wherein the two-photon-absorbing chromophore comprises sodium fluorescein or riboflavin.

11. The method of claim 8, wherein the ocular tissue comprises tissue of a lens.

12. The method of claim 8, wherein the ocular tissue comprises tissue of a cornea.

13. The method of claim 8, wherein the multiple-photon-absorbing chromophore is injected into a space formed by removal of the predetermined lenticule separated from the surrounding corneal material within the cornea in step (a).

14. The method of claim 1, wherein in step (b) locations defined by the focus spot are selected to form a structure selected from the group consisting of Bragg gratings, microlens arrays, zone plates, diffractive multifocals and Fresnel lenses.

15. The method of claim 1, wherein in step (b) the laser pulses are emitted at a frequency between 1 MHz and 10 GHz.

16. The method of claim 15, wherein in step (b) the laser frequency is between 10 MHz and 500 MHz.

17. The method of claim 1, wherein in step (b) the pulse width is between 10 fs and 100 fs.

18. The method of claim 1, wherein in step (b) the laser pulses have an average power between 1 mW and 1,000 mW.

19. The method of claim 1, wherein in step (b) the laser pulses have a pulse energy between 0.01 nJ and 10 nJ.

20. The method of claim 19, wherein in step (b) the laser pulses have a pulse energy between 0.1 and 2 nJ.

21. The method of claim 1, wherein in step (b) the size of the focus spot is between 0.5μ and 2μ.

22. The method of claim 1, wherein in step (b) the focus spot is scanned at a scanning speed between 0.4 μ/s and 1 m/s.

23. The method of claim 1, wherein in step (b) the focus spot is scanned at a scanning speed between 1 mm/s and 800 mm/s.

24. The method of claim 1, wherein in step (b) the focus spot is scanned at a scanning speed between 100 mm/s and 600 m/s.

25. The method of claim 1, wherein in step (b) the focus spot is scanned at a scanning speed of at least 1 mm/s.

26. The method of claim 1, wherein in step (b) the focus spot is scanned at a scanning speed of at least 100 mm/s.

27. The method of claim 1, wherein in step (b) the laser pulses have a wavelength between 600 and 1,000 nm.

28. The method of claim 27, wherein in step (b) the wavelength is between 700 and 900 nm.

29. The method of claim 1, wherein in step (b) the laser pulses have a wavelength between 1,000 and 1,300 nm.

30. The method of claim 1, wherein in step (b) the laser pulses have a wavelength between 350 and 600 nm.

31. The method of claim 1, wherein the diagnostics performed between steps (a) and (b) to determine further refinements to sphere, cylinder or higher order aberrations to be corrected in step (b) comprise wavefront aberrometry diagnostics.

\* \* \* \* \*